US007622257B2

(12) United States Patent
Tully et al.

(10) Patent No.: US 7,622,257 B2
(45) Date of Patent: Nov. 24, 2009

(54) SCREENING METHOD FOR STAUFEN ACTIVITY IN NEURONS

(75) Inventors: Timothy P. Tully, Cold Spring Harbor, NY (US); Roderick E. M. Scott, New York, NY (US); Rusiko Bourtchouladze, New York, NY (US)

(73) Assignee: Helicon Therapeutics, Inc., San Diego, CA (US)

( * ) Notice: Subject to any disclaimer, the term of this patent is extended or adjusted under 35 U.S.C. 154(b) by 0 days.

(21) Appl. No.: 12/023,870

(22) Filed: Jan. 31, 2008

(65) Prior Publication Data

US 2008/0160534 A1 Jul. 3, 2008

Related U.S. Application Data

(60) Division of application No. 11/020,026, filed on Dec. 21, 2004, now abandoned, which is a continuation of application No. PCT/US03/20125, filed on Jun. 25, 2003.

(60) Provisional application No. 60/391,687, filed on Jun. 25, 2002.

(51) Int. Cl.
C12Q 1/68 (2006.01)
C12N 5/00 (2006.01)
(52) U.S. Cl. .......................................... 435/6; 435/325
(58) Field of Classification Search ................. 435/325, 435/6
See application file for complete search history.

(56) References Cited

U.S. PATENT DOCUMENTS 5,824,837 A * 10/1998 Chen et al. .................... 800/3

FOREIGN PATENT DOCUMENTS

| CA | 2 238 656 | 11/1999 |
| WO | 99/51255 | 10/1999 |
| WO | WO 2004/001385 A2 | 12/2003 |

OTHER PUBLICATIONS

Dubnau, J et al., "The Staufen/Pumilio Pathway is Involved in Drosophila Long-Term Memory" Current Biology, vol. 13, No. 4, (Feb. 18, 2003), pp. 286-296, XP002394137 ISSN: 1059-1524.
Duchaîne, T., et al., "A Novel Murine Staufen Isoform Modulates the RNA Content of Staufen Complexes," *Mol. Cell Biol.* 20(15):5592-5601 (2000).
Kiebler, M.A., et al., "The Mammalian Staufen Protein Localizes to the Somatodendritic Domain of Cultured Hippocampal Neurons: Implications for Its Involvement in mRNA Transport," *J. Neurosci.* 19(1):288-297 (1999).
Köhrmann, M., et al., "Microtubule-dependent Recruitment of Staufen-Green Fluorescent Protein into Large RNA-containing Granules and Subsequent Dendritic Transport in Living Hippocampal Neurons," *Mol. Biol. Cell* 10: 2945-2953 (1999).
Monshausen, M., et al., "Two Rat Brain Staufen Isoforms Differentially Bind RNA," *J. Neurochem.* 76(1):155-165 (2001).
Tang, S.J., et al., "A Role for a Rat Homolog of Staufen in the Transport of RNA to Neuronal Dendrites," *Neuron* 32(3):463-475 (2001).
Steward, O., and Schuman, E.M., "Protein Synthesis at Synaptic Sites on Dendrites," *Annu. Rev. Neurosci.* 24:299-325 (2001).
Abel, T., et al., "Genetic Demonstration of a Role for PKA in the Late Phase of LTP and in Hippocampus-Based Long-Term Memory," *Cell* 88:615-626 (1997).
Raucher, D., et al., "Phosphatidylinositol 4,5-Bisphosphate Functions as a Second Messenger that Regulates Cytoskeleton-Plasma Membrane Adhesion," *Cell* 100:221-228 (2000).
Li, P., et al., "Inscuteable and Staufen Mediate Asymmetric Localization and Segregation of *prospero* RNA during Drosophila Neuroblast Cell Divisions," *Cell* 90:437-447 (1997).
Ephrussi, A. and Lehmann, R., "Induction of Germ Cell Formation by *oskar*," *Nature* 358:387-392 (1992).
Huber, K.M., et al., "Role for Rapid Dendritic Protein Synthesis in Hippocampal mGluR-Dependent Long-Term Depression," *Science* 288:1254-1256 (2000).
Giese, K.P., et al., "Autophosphorylation at Thr$^{286}$ of the α Calcium-Calmodulin Kinase II in LTP and Learning," *Science* 279:870-873 (1998).
O'Keefe, J. and Nadel, L., "Discrimination and Maze Learning," in *The Hippocampus as a Cognitive Map* (Oxford: Oxford University Press), pp. 288-290 (1978).
Moser, M.-B., et al., "Spatial Learning with a Minislab in the Dorsal Hippocampus," *Proc. Natl. Acad. Sci. USA* 92:9697-9701 (1995).
Squire, L.R., "Memory and the Hippocampus: A Synthesis From Findings With Rats, Monkeys, and Humans," *Psychol. Rev.* 99 (2):195-231 (1992).
Steward, O. and Levy, W.B., "Preferential Localization of Polyribosomes Under the Base of Dendritic Spines in Granule Cells of the Dentate Gyrus," *J. Neurosci.* 2(3):284-291 (1982).
Scott, R., at al., "CREB and the Discovery of Cognitive Enhancers," *J. Mol. Neurosci.* 19:171-177 (2002).
Schuman, E.M., "mRNA Trafficking and Local Protein Synthesis at the Synapse," *Neuron* 23:645-648 (1999).
Phillips, R.G. and LeDoux, J.E., "Differential Contribution of Amygdala and Hippocampus to Cued and Contextual Fear Conditioning," *Behav. Neurosci.* 106(2):274-285 (1992).
Kogan, J.H., et al., "Spaced Training Induces Normal Long-Term Memory in CREB Mutant Mice," *Curr. Biol.* 7(1):1-11 (1996).
Silva, A.J., et al. "Impaired Learning in Mice With Abnormal Short-Lived Plasticity," *Curr. Biol.* 6(11):1509-1518 (1996).
Logue, S. F., et al., "Hippocampal Lesions Cause Learning Deficits in Inbred Mice in the Morris Water Maze and Conditioned-Fear Task," *Behav. Neurosci.* 111(1):104-113 (1997).

(Continued)

*Primary Examiner*—Valarie Bertoglio
*Assistant Examiner*—Marcia S Noble
(74) *Attorney, Agent, or Firm*—Sheppard, Mullin, Richter & Hampton LLP

(57) ABSTRACT

The present invention provides cell-based screening methods for identifying pharmaceutical agents which are capable of modulating (have the ability to modulate) STAUFEN function by screening for STAUFEN function.

5 Claims, 4 Drawing Sheets

OTHER PUBLICATIONS

Kim, J.J., et al., "Effects of Amygdala, Hippocampus, and Periaqueductal Gray Lesions on Short- and Long-Term Contextual Fear," *Behav. Neurosci.* 107(6):1093-1098 (1993).

Holland, P.C. and Bouton, M.E., "Hippocampus and Context in Classical Conditioning," *Curr. Opin. Neurobiol.* 9(2):195-202 (1999).

Frankland, P.W., et al., "The Dorsal Hippocampus is Essential for Context Discrimination but Not for Contextual Conditioning," *Behav. Neurosci.* 112(4):863-874 (1998).

Chen, C., et al., "Hippocampal Lesions Impair Contextual Fear Conditioning in Two Strains of Mice," *Behav. Neurosci.* 110(5):1177-1180 (1996).

Jarrard, L.E., "On the Role of the Hippocampus in Learning and Memory in the Rat," *Behav. Neural. Biol.* 60:9-26 (1993).

Barnes, C.A., et al., "Hippocampal Synaptic Enhancement as a Basis for Learning and Memory: A Selected Review of Current Evidence From Behaving Animals," In *Brain and Memory, Modulation and Mediation of Neuroplasticity*, J. L. McGaugh, et al., eds. (New York: Oxford University Press), pp. 259-276 (1995).

Burgess, N., et al., "Predictions Derived From Modelling the Hippocampal Role in Navigation," *Biol. Cybern.* 83:301-312 (2000).

O'Keefe, J., "Do Hippocampal Pyramidal Cells Signal Non-Spatial as Well as Spatial Information?," *Hippocampus* 9:352-364 (1999).

Milner, B., et al., "Cognitive Neuroscience and the Study of Memory," *Neuron* 20:445-468 (1998).

Morris, R.G.M., et al., "Place Navigation Impaired in Rats With Hippocampal Lesions," *Nature* 297:681-683 (1982).

Casadio, A., et al., "A Transient, Neuron-Wide Form of CREB-Mediated Long-Term Facilitation Can Be Stabilized at Specific Synapses by Local Protein Synthesis," *Cell* 99:221-2378 (1999).

\* cited by examiner

```
                              SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Antisense oligodeoxynucleotides

<400> SEQUENCE: 1
tsgsgstcat ttgttaccgs gstsg                                        25

<210> SEQ ID NO 2
<211> LENGTH: 26
<212> TYPE: DNA
<213> ORGANISM: Artificial Sequence
<220> FEATURE:
<223> OTHER INFORMATION: Antisense oligodeoxynucleotides

<400> SEQUENCE: 2
gstscstgta gtcgatctat sgsgst                                       26

<210> SEQ ID NO 3
<211> LENGTH: 23
<212> TYPE: DNA
<213> ORGANISM: Artificial Sequence
<220> FEATURE:
<223> OTHER INFORMATION: Antisense oligodeoxynucleotides

<400> SEQUENCE: 3
gsgsgsctta tacattgsgs tst                                          23
```

<210> SEQ ID NO 4
<211> LENGTH: 23
<212> TYPE: DNA
<213> ORGANISM: Artificial Sequence
<220> FEATURE:
<223> OTHER INFORMATION: Antisense oligodeoxynucleotides

<400> SEQUENCE: 4
gstsgstact gattgacsts gst                                              23

<210> SEQ ID NO 5
<211> LENGTH: 42
<212> TYPE: DNA
<213> ORGANISM: Artificial Sequence
<220> FEATURE:
<223> OTHER INFORMATION: Oligo-DT primer containing T7 RNA polymerase
      sequence
<220> FEATURE:
<221> NAME/KEY: misc_feature
<222> LOCATION: 42
<223> OTHER INFORMATION: n = A, T, C or G

<400> SEQUENCE: 5
ggccagtgaa ttgtaatacg actcactata gggaggcggt vn                         42

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
tgtagacata gtctggggtc ctc                                              23

<210> SEQ ID NO 7
<211> LENGTH: 22
<212> TYPE: DNA
<213> ORGANISM: Artificial Sequence
<220> FEATURE:
<223> OTHER INFORMATION: PCR Primer

<400> SEQUENCE: 7
aagcaacagc cattgggtcc ac                                               22

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gcaactcgtc ggcggcatc                                                   19

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
cgccgggccg ttgtactttg t                                                21

```
<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
ccactctgat tccgccactg                                               20

<210> SEQ ID NO 11
<211> LENGTH: 22
<212> TYPE: DNA
<213> ORGANISM: Artificial Sequence
<220> FEATURE:
<223> OTHER INFORMATION: PCR Primer

<400> SEQUENCE: 11
gcgttgaatc ctcctcggta tc                                            22

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
gcggctgtga ttatgcgaat                                               20

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
catactttct cgctgccagt ctg                                           23

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14
cagactaccg atgcgaacaa ca                                            22

<210> SEQ ID NO 15
<211> LENGTH: 23
<212> TYPE: DNA
<213> ORGANISM: Artificial Sequence
<220> FEATURE:
<223> OTHER INFORMATION: PCR Primer

<400> SEQUENCE: 15
gtgcctgaac tggtggtgta tca                                           23

<210> SEQ ID NO 16
<211> LENGTH: 20
<212> TYPE: DNA
<213> ORGANISM: Artificial Sequence
<220> FEATURE:
<223> OTHER INFORMATION: PCR Primer
```

-continued

```
<400> SEQUENCE: 16
cgccttctgg aggcaatact                                                        20

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
gcgatctgta gtggctcctt g                                                      21

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
cactcgcact tattgcaagc atacg                                                  25
```

SCREENING METHOD FOR STAUFEN ACTIVITY IN NEURONS

CROSS-REFERENCE TO RELATED APPLICATIONS

This application is a divisional application of U.S. application Ser. No. 11/020,026, filed Dec. 21, 2004 now abandoned which is a continuation application of International Application No. PCT/US2003/020125, which designated the United States and was filed Jun. 25, 2003, published in English, which claims the benefit of U.S. Provisional Application No. 60/391,687, filed Jun. 25, 2002. The entire teachings of the above applications are incorporated herein by reference.

BACKGROUND OF THE INVENTION

Long term memory (LTM) involves induction of a cascade of gene expression (Davis, H. P. and Squire, L. R., Psychol. Bull., 96:518-559 (1984); Tully, T. et al., Cell, 79:35-47 (1994); Yin, J. C. et al., Cell, 79:49-58 (1994); Yin, J. C. et al., Cell, 81:107-115 (1995); Josselyn, S. A. et al., J. Neurosci., 21:2404-2412 (2001); Alberini, C. M. et al., Cell, 76:1099-1114 (1994); and Taubenfeld, S. M. et al., J. Neurosci., 21:84-91 (2001)) under control of the CREB transcription factor (Davis, H. P. and Squire, L. R., Psychol. Bull., 96:518-559 (1984); Tully, T. et al., Cell, 79:35-47 (1994); Yin, J. C. et al., Cell, 79:49-58 (1994); Yin, J. C. et al., Cell, 81:107-115 (1995); Josselyn, S. A. et al., J. Neurosci., 21:2404-2412 (2001); Alberini, C. M. et al., Cell, 76:1099-1114 (1994); and Taubenfeld, S. M. et al., J. Neurosci., 21:84-91 (2001)), which leads to structural and functional changes in specific synapses (Bartsch, D. et al., Cell, 83:979-992 (1995); and Dash, P. K. et al., Nature, 345:718-721 (1990)). LTM is disrupted by induced over-expression of a CREB repressor transgene in flies (Yin, J. C. et al., Cell, 79:49-58 (1994)), by partial knock-out of CREB in mice (Bourtchuladze, R. et al., Cell, 79:59-68 (1994)), by knock-down of CREB with anti-sense RNA in rats (Guzowski, J. F. and McGaugh, J. L., Proc. Natl. Acad. Sci. USA, 94:2693-2698 (1997); and Lamprecht, R. et al., J. Neurosci., 17:8443-8450 (1997)) or by induced over expression of a dominant-negative CREB in mice (Kida, S. et al., Nat. Neurosci., 5:348-355 (2002); and Pittenger, C. et al., Neuron, 34:447-462 (2002)). Synaptic plasticity is disrupted similarly in Aplysia (Bartsch, D. et al., Cell, 83:979-992 (1995)), in flies (Davis, G. W. et al., Neuron, 17:669-679 (1996); and Sanyal, S. et al., Nature, 416:870-874 (2002)) and in mice (Bourtchuladze, R. et al., Cell, 79:59-68 (1994); Barco, A. et al., Cell, 108:689-703 (2002); and Casadio, A. et al., Cell, 99:221-237 (1999)). Strikingly, over expression of CREB activator in transgenic flies, or in virus-infected rats, enhances LTM (Yin, J. C. et al., Cell, 81:107-115 (1995); and Josselyn, S. A. et al., J. Neurosci., 21:2404-2412 (2001)), while analogous modulations of CREB activator enhance (i) long-term facilitation (LTF) and the concomitant growth of synaptic connections in sensorimotor neuron co-cultures of Aplysia (Bartsch, D. et al., Cell, 83:979-992 (1995)) and (ii) long-term potentiation (LTP) in rat hippocampus (Barco, A. et al., Cell, 108:689-703 (2002)). These convergent data establish that long-term memory (LTM) formation requires gene transcription (Yin, J. C. et al., Cell, 81:107-115 (1995); Abel, T. et al., Science, 279:338-341 (1998); and Tully, T., Proc. Natl. Acad. Sci. USA, 94:4239-4241 (1997)).

This insight has raised two new questions. First, specifically what genes are regulated during LTM formation? Attempts to answer this question have been pursued with in vitro models of neuronal plasticity, with strong pharmacological stimulation in vivo and, in a few cases, with behavioral training (Cole, A. J. et al., Nature, 340:474-476 (1989); Hevroni, D. et al., J. Mol. Neurosci., 10:75-98 (1998); Irwin, L. N., Brain Res. Mol. Brain. Res., 96:163-169 (2001); Luo, Y. et al., J. Mol. Neurosci., 17:397-404 (2001); Cavallaro, S. et al., Eur. J. Neurosci., 13:1809-1815 (2001); Nedivi, E. et al., Nature, 363:718-722 (1993); and Nedivi, E. et al., Proc. Natl. Acad. Sci. USA, 93:2048-2053 (1996)). Second, how does a transcriptional response in the cell nucleus tag only a subset of synapses involved in LTM (Barco, A. et al., Cell, 108:689-703 (2002); Casadio, A. et al., Cell, 99:221-237 (1999); Frey, U. and Morris, R. G., Nature, 385:533-536 (1997); Martin, K. C. et al., Cell, 91:927-938 (1997); Steward, O. et al., Neuron, 21:741-751 (1998); Steward, O. and Schuman, E. M., Annu. Rev. Neurosci., 24:299-325 (2001); Steward, O. and Worley, P. F., Proc. Natl. Acad. Sci. USA, 98:7062-7068 (2001); Steward, O. and Worley, P. F., Neuron, 30:227-240 (2001); and Steward, O. and Worley, P., Results Probl. Cell. Differ., 34:1-26 (2001)) Thus far, analyses of in vitro models of synaptic plasticity have described the cellular phenomenology of synapse specific modification but have not yet identified the cellular machinery or established a connection to memory.

SUMMARY OF THE INVENTION

It has been discovered that STAUFEN plays an important role in mediating the cellular events underlying memory formation in mammals. As described herein, STAUFEN-mediated mRNA trafficking within the hippocampus has been discovered to be important for contextual long-term memory formation in mammals. It has been discovered that disruption of hippocampal STAUFEN function impairs long term memory formation in mammals.

The present invention provides cell-based screening methods for identifying pharmaceutical agents which are capable of modulating (have the ability to modulate) STAUFEN function by screening for STAUFEN function. In one embodiment, STAUFEN function is screened by determining the level of STAUFEN protein expression (translation). As described herein, STAUFEN is transcriptionally upregulated during memory formation. Accordingly, in this embodiment, STAUFEN protein expression can be determined by determining STAUFEN mRNA or protein production. In a second embodiment, STAUFEN function is screened by determining the functional readout of STAUFEN. In this embodiment, a functional readout of STAUFEN can be determined by detecting (such as using an antibody) the translocation of the STAUFEN into dendrites or by determining the level of STAUFEN protein production. A functional readout of STAUFEN can also be determined indirectly by detecting and measuring downstream gene products regulated by a staufen gene product. In a third embodiment, STAUFEN function is screened by determining the change in distribution of neural granules in the cells.

By "STAUFEN function" is meant the biological activity of STAUFEN, which includes subcellular translocation of various mRNAs and local regulation of various protein translations ("the STAUFEN pathway"). Biological activity is understood to mean biological function or action. By "STAUFEN pathway function" is meant a set of gene products which interact with a staufen gene product and/or with each other to produce STAUFEN function, particularly the subcellular translocation of mRNA and local regulation of protein translation.

In a particular embodiment, STAUFEN::indicator fusion protein constructs are employed in cell-based screening methods for identifying a pharmaceutical agent which is capable of modulating STAUFEN function. Thus, in one embodiment, a cell-based screening method for identifying a pharmaceutical agent which is capable of modulating STAUFEN function comprises (a) introducing a pharmaceutical agent of interest into host cells (particularly cells of neural origin) expressing a STAUFEN::indicator fusion protein (e.g., STAUFEN::GFP fusion protein); and (b) determining STAUFEN function. In a particular embodiment, the pharmaceutical agent is introduced into cells after stimulation of the CREB pathway using forskolin, for example. By CREB pathway function is meant CREB-dependent gene expression. The STAUFEN function determined in (b) is compared to the STAUFEN function of the host cells of (a) to which the pharmaceutical agent has not been introduced (untreated host cells expressing STAUFEN::indicator fusion protein) (control). A difference in STAUFEN function determined in the treated cells relative to the STAUFEN function of untreated cells identifies the pharmaceutical agent as one which modulates (or is capable of modulating) STAUFEN function. In one embodiment, STAUFEN function is determined by detecting and determining the level of STAUFEN::indicator fusion protein expression (translation) (e.g., by detecting STAUFEN::indicator fusion protein mRNA or protein production). In a second embodiment, STAUFEN function is determined by detecting (such as using an antibody) the translocation of the STAUFEN::indicator fusion protein into dendrites or by determining the level of STAUFEN::indicator fusion protein production. In a third embodiment, STAUFEN function is determined indirectly by detecting and measuring downstream gene products regulated by a staufen gene product. In a fourth embodiment, STAUFEN function is determined by determining the change in distribution of neural granules in the cells.

Pharmaceutical agents which modulate, or are capable of modulating, STAUFEN function are further screened to determine the effect of the agents on long term memory formation or to identify those agents capable of modulating long term memory. In one embodiment, the method comprises (a) administering to an animal (particularly a mammal) a pharmaceutical agent which modulates, or is capable of modulating, STAUFEN function; (b) training the animal of (a) and a control animal of the same species to which the pharmaceutical has not been administered under conditions sufficient to produce long term memory formation in the animals; (c) assessing long term memory formation in the animals trained in step (b); and (d) comparing long term memory formation in the animals assessed in step (c). A control animal is the basis for comparison in assessing results associated with administration of a pharmaceutical agent to an experimental animal. The experimental and control animals are comparable, e.g., same age, genetic makeup, basal STAUFEN function (i.e., STAUFEN function prior to treatment with the pharmaceutical agent). A difference in long term memory formation assessed in the animal treated with (administered) the pharmaceutical agent relative to the long term memory formation assessed in the control animal identifies the pharmaceutical agent as one which has the ability to modulate long term memory formation in the animal.

Pharmaceutical agents which modulate, or are capable of modulating, STAUFEN function are also screened to determine the effect of the agents on performance by an animal of a hippocampal-dependent cognitive task or to identify those agents capable of modulating performance of a hippocampal-dependent cognitive task by an animal. In one embodiment, the method comprises (a) administering to an animal (particularly a mammal) a pharmaceutical agent which modulates, or is capable of modulating, STAUFEN function; (b) training the animal of (a) and a control animal of the same species to which the pharmaceutical agent has not been administered under conditions appropriate for performance by the animals of a specified hippocampal-dependent cognitive task; (c) assessing performance of the hippocampal-dependent cognitive task by the animals trained in step (b); and (d) comparing performance of the animals assessed in step (c). The experimental and control animals are comparable, e.g., same age, genetic makeup, basal STAUFEN function (i.e., STAUFEN function prior to treatment with the pharmaceutical agent). A difference in assessed performance by the animal treated with (administered) the pharmaceutical agent relative to the assessed performance by the control animal identifies the pharmaceutical agent as one which has the ability to modulate the performance by the animal of the specified hippocampal-dependent cognitive task.

The present invention also provides methods of screening a pharmaceutical agent for its ability to modulate long term memory formation in a mammal, preferably an adult mammal, comprising (a) administering a pharmaceutical agent of interest to a first mammal; (b) determining STAUFEN function in the mammal administered the pharmaceutical agent (a) relative to STAUFEN function in a control mammal of the same species as the first mammal to which the pharmaceutical agent has not been administered; (c) selecting the pharmaceutical agent if the STAUFEN function determined in (b) differs from the STAUFEN function in the control mammal; (d) administering the pharmaceutical agent selected in (c) to a second mammal; (e) training the second mammal administered the pharmaceutical agent (d) and a control mammal of the same species as the second mammal under conditions appropriate to produce long term memory formation in the mammals; (f) assessing long term memory formation in the mammals trained in step (e); and (g) comparing long term memory formation in the mammals assessed in step (f). The first and second mammals can be of the same or different species. The first mammal and the corresponding control mammal are comparable, e.g., same age, genetic makeup, basal STAUFEN function (i.e., STAUFEN function prior to treatment with the pharmaceutical agent). Similarly, the second mammal and the corresponding control mammal are comparable, e.g., same age, genetic makeup, basal STAUFEN function (i.e., STAUFEN function prior to treatment with the pharmaceutical agent). A difference in long term memory formation assessed in the mammal treated with the pharmaceutical agent relative to the long term memory formation assessed in the control mammal identifies the pharmaceutical agent as one which has the ability to modulate long term memory formation in the mammal.

The present invention further provides methods of screening a pharmaceutical agent for its ability to modulate STAUFEN function in a mammal, preferably an adult mammal, comprising (a) administering a pharmaceutical agent of interest to a mammal; and (b) determining STAUFEN function in the mammal administered the pharmaceutical agent (a) relative to STAUFEN function in a control mammal of the same species to which the pharmaceutical agent has not been administered. The experimental and control mammals are comparable, e.g., same age, genetic makeup, basal STAUFEN function (i.e., STAUFEN function prior to treatment with pharmaceutical agent). A difference in STAUFEN function determined in the mammal treated with the pharmaceutical agent relative to STAUFEN function determined in the control mammal identifies the pharmaceutical agent as one having the ability to modulate STAUFEN function in the mammal.

The invention further relates to methods for assessing the effect of a pharmaceutical agent on long term memory formation in a mammal, preferably an adult mammal, comprising (a) administering a pharmaceutical agent of interest to a first mammal; (b) determining STAUFEN function in the mammal administered the pharmaceutical agent (a) relative to STAUFEN function in a control mammal of the same species as the first mammal to which the pharmaceutical agent has not been administered; (c) selecting the pharmaceutical agent if the STAUFEN function determined in (b) differs from the STAUFEN function in the control mammal; (d) administering the pharmaceutical agent selected in (c) to a second mammal; (e) training the second mammal administered the pharmaceutical agent in (d) a control mammal of the same species as the second mammal under conditions appropriate to produce long term memory formation in the mammals; (f) assessing long term memory formation in the mammals trained in step (e); and (g) comparing long term memory formation in the mammals assessed in step (f). The first and second mammals can be of the same or different species. The first mammal and the corresponding control mammal are comparable, e.g., same age, genetic makeup, basal STAUFEN function (i.e., STAUFEN function prior to treatment with the pharmaceutical agent). Similarly, the second mammal and the corresponding control mammal are comparable, e.g., same age, genetic makeup, basal STAUFEN function (i.e., STAUFEN function prior to treatment with the pharmaceutical agent). A difference in long term memory formation assessed in the mammal treated with the pharmaceutical agent relative to the long term memory formation assessed in the control mammal identifies the pharmaceutical agent as one having an effect on long term memory formation in the mammal.

The invention also relates to methods of assessing the effect of a pharmaceutical agent on STAUFEN function in a mammal, preferably an adult mammal, comprising (a) administering a pharmaceutical agent of interest to the mammal; and (b) determining STAUFEN function in the mammal administered the pharmaceutical agent in (a) relative to STAUFEN function in a control mammal of the same species to which the pharmaceutical agent has not been administered. The experimental and control mammals are comparable, e.g., same age, genetic makeup, basal STAUFEN function (i.e., STAUFEN function prior to treatment with pharmaceutical agent). A difference in STAUFEN function determined in the mammal treated with the pharmaceutical agent relative to STAUFEN function determined in the control mammal identifies the pharmaceutical agent as one having an effect on STAUFEN function in the mammal.

The invention also relates to methods of screening a pharmaceutical agent for its ability to modulate performance of a hippocampal-dependent cognitive task by a mammal, preferably an adult mammal, comprising (a) administering a pharmaceutical agent of interest to a first mammal; (b) determining STAUFEN function in the mammal administered the pharmaceutical agent (a) relative to STAUFEN function in a control mammal of the same species as the first mammal to which the pharmaceutical agent has not been administered; (c) selecting the pharmaceutical agent if STAUFEN function determined in (b) differs from the STAUFEN function in the control mammal; (d) administering the pharmaceutical agent selected in (c) to a second mammal; (e) training the mammal administered the pharmaceutical agent in (d) a control mammal of the same species as the second mammal under conditions appropriate for performance by the mammals of a specified hippocampal-dependent cognitive task; (f) assessing performance of the hippocampal-dependent cognitive task by the mammals trained in step (e); and (g) comparing performance of the hippocampal-dependent cognitive task by the mammals assessed in step (f). The first and second mammals can be of the same or different species. The first mammal and the corresponding control mammal are comparable, e.g., same age, genetic makeup, basal STAUFEN function (i.e., STAUFEN function prior to treatment with the pharmaceutical agent). Similarly, the second mammal and the corresponding control mammal are comparable, e.g., same age, genetic makeup, basal STAUFEN function (i.e., STAUFEN function prior to treatment with the pharmaceutical agent). A difference in assessed performance by the mammal treated with the pharmaceutical agent relative to the assessed performance by the control mammal identifies the pharmaceutical agent as one which has the ability to modulate the performance by the mammal of the specified hippocampal-dependent cognitive task.

The invention further relates to methods for assessing the effect of a pharmaceutical agent on performance of a hippocampal-dependent cognitive task by a mammal, preferably an adult mammal, comprising (a) administering a pharmaceutical agent of interest to a first mammal; (b) determining STAUFEN function in the mammal administered the pharmaceutical agent in (a) relative to STAUFEN function in a control mammal of the same species as the first mammal to which the pharmaceutical agent has not been administered; (c) selecting the pharmaceutical agent if the STAUFEN function determined in (b) differs from the STAUFEN function in the control mammal; (d) administering the pharmaceutical agent selected in (c) to a second mammal; (e) training the mammal administered the pharmaceutical agent in step (d) and a control mammal of the same species as the second mammal under conditions appropriate for performance by the mammals of a specified hippocampal-dependent cognitive task; (f) assessing performance of the hippocampal-dependent cognitive task by the mammals trained in step (e); and (g) comparing the performance of the hippocampal-dependent cognitive task by the mammals assessed in step (f). The first and second mammals can be of the same or different species. The first mammal and the corresponding control mammal are comparable, e.g., same age, genetic makeup, basal STAUFEN function (i.e., STAUFEN function prior to treatment with the pharmaceutical agent). Similarly, the second mammal and the corresponding control mammal are comparable, e.g., same age, genetic makeup, basal STAUFEN function (i.e., STAUFEN function prior to treatment with the pharmaceutical agent). A difference in assessed performance by in the mammal treated with the pharmaceutical agent relative to the assessed performance by the control mammal identifies the pharmaceutical agent as one having an effect on performance by the mammal of the specified hippocampal-dependent cognitive task.

Training can comprise one or multiple training sessions and is training appropriate for long term memory formation or for performance of the specified cognitive task. The pharmaceutical agent can be administered before, during or after one or more training sessions.

The invention also provides methods for modulating long term memory formation in a mammal. In a particular embodiment, the mammal is an adult mammal. In one embodiment, the method comprises treating the mammal to modulate staufen-dependent protein expression. In a second embodiment, the method comprises treating the mammal to modulate STAUFEN function. In a particular embodiment, the method comprises administering to the mammal an effective amount of a pharmaceutical agent which modulates STAUFEN function in the mammal. In another embodiment, the method comprises treating the mammal to modulate STAUFEN protein expression. In a particular embodiment, the method comprises administering to the mammal an effective amount of a pharmaceutical agent which modulates STAUFEN protein expression in the mammal.

The present invention also provides methods for enhancing long term memory formation in a mammal. In a particular embodiment, the mammal is an adult mammal. In one embodiment, the method comprises treating the mammal to modulate staufen-dependent protein expression. In a second embodiment, the method comprises treating the mammal to increase STAUFEN function relative to the STAUFEN function in the mammal prior to treatment. In a particular embodiment, treatment to increase STAUFEN function comprises administering to the mammal an effective amount of a pharmaceutical agent which increases STAUFEN function relative to STAUFEN function in the mammal prior to administration of the pharmaceutical agent. In another embodiment, the method comprises treating the mammal to increase STAUFEN protein expression relative to STAUFEN protein expression in the mammal prior to treatment. In a particular embodiment, treatment to increase STAUFEN protein expression comprises administering to the mammal an effective amount of a pharmaceutical agent which increases STAUFEN protein expression relative to STAUFEN protein expression in the mammal prior to administration of the pharmaceutical agent. In still another embodiment, the method comprises administering to the mammal an effective amount of exogenous STAUFEN, STAUFEN analog, biologically active STAUFEN fragment or STAUFEN fusion protein. In yet another embodiment, the method comprises administering to the mammal an effective amount of a nucleic acid sequence encoding exogenous STAUFEN, STAUFEN analog, biologically active STAUFEN fragment or STAUFEN fusion protein.

The present invention further provides methods for treating a mammal with a defect in long term memory formation associated with a defect in STAUFEN. The mammal is preferably an adult mammal. The defect in STAUFEN is either a diminution in the amount of STAUFEN produced, a diminution in STAUFEN function of STAUFEN produced or both a diminution in amount of STAUFEN produced and STAUFEN function of STAUFEN produced. In one embodiment, the method comprises treating a mammal with a defect in long term memory formation associated with a defect in STAUFEN to increase STAUFEN function relative to the STAUFEN function in the mammal prior to treatment. In a particular embodiment, treatment to increase STAUFEN function comprises administering to the mammal an effective amount of a pharmaceutical agent which increases STAUFEN function relative to STAUFEN function in the mammal prior to administration of the pharmaceutical agent. In a second embodiment, the method comprises treating a mammal with a defect in long term memory formation associated with a defect in STAUFEN to increase STAUFEN protein expression relative to STAUFEN protein expression in the mammal prior to treatment. In a particular embodiment, treatment to increase STAUFEN protein expression comprises administering to the mammal an effective amount of a pharmaceutical agent which increases STAUFEN protein expression relative to STAUFEN protein expression in the mammal prior to administration of the pharmaceutical agent. In a another embodiment, the method comprises administering to a mammal with a defect in long term memory formation associated with a defect in STAUFEN, a STAUFEN compound such as exogenous STAUFEN, STAUFEN analog, biologically active STAUFEN fragment or STAUFEN fusion protein. In still another embodiment, the method comprises administering to a mammal with a defect in long term memory formation with a defect in STAUFEN, a nucleic acid sequence encoding exogenous STAUFEN, STAUFEN analog, biologically active STAUFEN fragment or STAUFEN fusion protein.

The invention also provides methods for modulating performance of a hippocampal-dependent cognitive task by a mammal. In a particular embodiment, the mammal is an adult mammal. In one embodiment, the method comprises treating the mammal to modulate staufen-dependent protein expression. In a second embodiment, the method comprises treating the mammal to modulate STAUFEN function. In a particular embodiment, the method comprises administering to the mammal an effective amount of a pharmaceutical agent which modulates STAUFEN function in the mammal. In another embodiment, the method comprises treating the mammal to modulate STAUFEN protein expression. In a particular embodiment, the method comprises administering to the mammal an effective amount of a pharmaceutical agent which modulates STAUFEN protein expression in the mammal.

The present invention provides methods for enhancing performance of a hippocampal-dependent cognitive task by a mammal. The mammal is preferably an adult mammal. In one embodiment, the method comprises treating the mammal to modulate staufen-dependent protein expression. In a second embodiment, the method comprises treating the mammal to increase STAUFEN function relative to STAUFEN function in the mammal prior to treatment. In a particular embodiment, treatment to increase STAUFEN function comprises administering to the mammal an effective amount of a pharmaceutical agent which increases STAUFEN function relative to STAUFEN function in the mammal prior to administration of the pharmaceutical agent. In another embodiment, the method comprises treating the mammal to increase STAUFEN protein expression relative to STAUFEN protein expression in the mammal prior to treatment. In a particular embodiment, treatment to increase STAUFEN protein expression comprises administering to the mammal an effective amount of a pharmaceutical agent which increases STAUFEN protein expression relative to STAUFEN protein expression in the mammal prior to administration of the pharmaceutical agent. In another embodiment, the method comprises administering to the mammal an effective amount of exogenous STAUFEN, STAUFEN analog, biologically active STAUFEN fragment or STAUFEN fusion protein. In still another embodiment, the method comprises administering to the mammal an effective amount of a nucleic acid sequence encoding exogenous STAUFEN, STAUFEN analog, biologically active STAUFEN fragment or STAUFEN fusion protein.

The present invention further provides methods for treating a mammal with a defect in performance of a hippocampal-dependent cognitive task, wherein the defect in performance is associated with a defect in STAUFEN. The mammal is preferably an adult mammal. The defect in STAUFEN is either a diminution in the amount of STAUFEN produced, a diminution in STAUFEN function of STAUFEN produced or both a diminution in amount of STAUFEN produced and STAUFEN function of STAUFEN produced. In one embodiment, the method comprises treating a mammal with a defect in performance of a hippocampal-dependent cognitive task associated with a defect in STAUFEN to increase STAUFEN function relative to STAUFEN function in the mammal prior to treatment. In a particular embodiment, treatment to increase STAUFEN function comprises administering to the mammal an effective amount of a pharmaceutical agent which increases STAUFEN function relative to STAUFEN function in the mammal prior to administration of the pharmaceutical agent. In a second embodiment, the method comprises treating a mammal with a defect in performance of a hippocampal-dependent cognitive task associated with a defect in STAUFEN to increase STAUFEN protein expression relative to STAUFEN protein expression in the mammal prior to treatment. In a particular embodiment, treatment to increase STAUFEN protein expression comprises administering to the mammal an effective amount of a pharmaceutical agent which increases STAUFEN protein expression relative to STAUFEN protein expression in the mammal prior to administration of the pharmaceutical agent. In another embodiment, the method comprises administering to a mammal with a defect in performance of a hippocampal-dependent cognitive task associated with a defect in STAUFEN, a STAUFEN compound such as exogenous STAUFEN, STAUFEN analog, biologically active STAUFEN fragment or STAUFEN fusion protein. In still another embodiment, the method comprises administering to a mammal with a defect in performance of a hippocampal-dependent cognitive task associated with a defect in STAUFEN, a nucleic acid sequence encoding exogenous STAUFEN, STAUFEN analog, biologically active STAUFEN fragment or STAUFEN fusion protein.

The invention also provides methods for modulating performance by a mammal of cognitive tasks associated with non-hippocampal regions of the brain where staufen gene expression is found to occur, methods for treating a defect in performance by an animal of cognitive tasks associated with non-hippocampal regions of the brain where staufen gene expression is found to occur and methods for screening a pharmaceutical agent for its ability to modulate performance by an animal of cognitive tasks associated with non-hippocampal regions of the brain where staufen gene expression is found to occur. Such methods are similar to the methods described herein for modulating performance by a mammal of hippocampal-dependent cognitive tasks, for treating a defect in performance by an animal of hippocampal-dependent cognitive tasks and for screening a pharmaceutical agent for its ability to modulate performance by an animal of hippocampal-dependent cognitive tasks.

BRIEF DESCRIPTION OF THE DRAWINGS

FIG. 7A shows that transcripts induced by spaced training are packaged into neural granules (GR) along with other functional components including stau, osk, faf and mago, which are required to translocate GR along microtubules (MT) into neuronal processes dendrites (Krichevsky, A. M.

and Kosik, K. S., *Neuron,* 32:683-696 (2001); Kiebler, M. A. et al., *J. Neurosci.,* 19:288-297 (1999); and Kohrmann, M. et al., *Mol. Biol. Cell.,* 10: 2945-2953 (1999)). Disassembly of GR and derepression of packaged mRNAs occur in response to depolarization (Krichevsky, A. M. and Kosik, K. S., *Neuron,* 32:683-696 (2001)).

Figure 7:
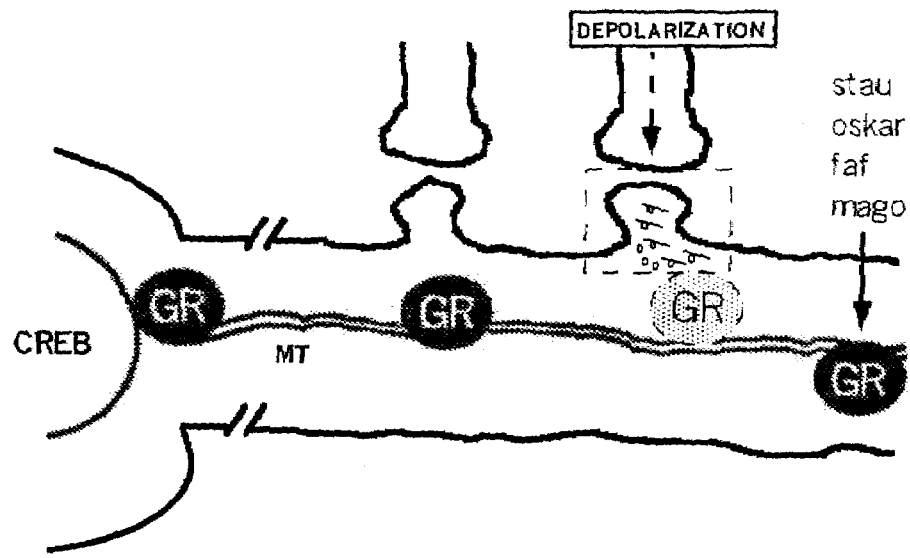
FIGS. 7A and 7B are schematic diagrams depicting a model described herein for synapse-specific modification underlying long-term memory.
Figure 7:
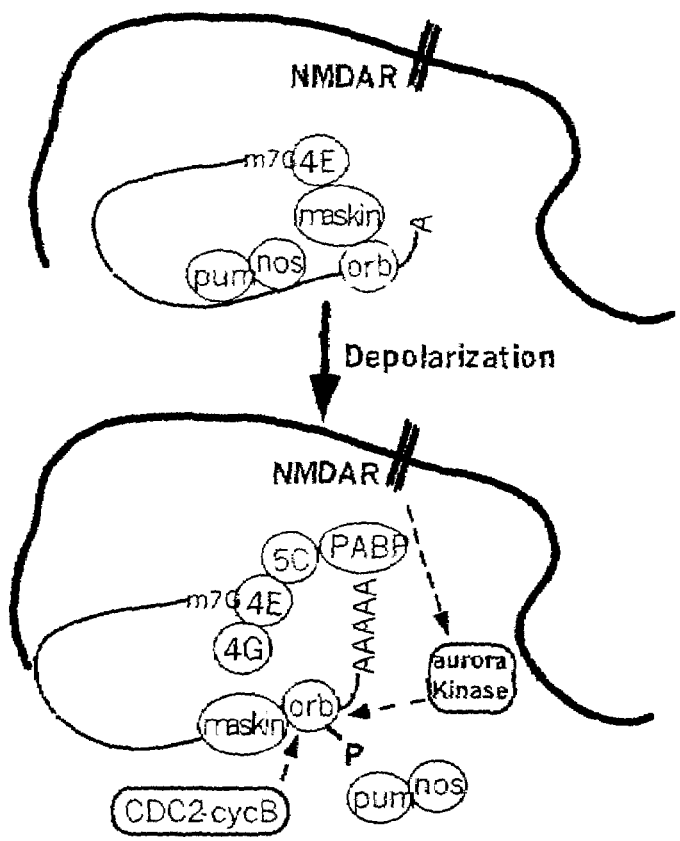

FIG. 7B shows detail of the boxed area from FIG. 7A. mRNAs packaged into GR are translationally repressed by RNA binding proteins, including PUM, NOS, MASKIN and (inactive) ORB. Synaptic depolarization stimulates local kinases, such as aurora kinase, cdc2-kinase (and perhaps others) to phosphorylate ORB. Activated ORB promotes elongation of polyA tail (Wu, L. et al., *Neuron,* 21:1129-1139 (1998)) and induces the release of eIF4E from MASKIN (Stebbins-Boaz, B. et al., *Mol. Cell.,* 4:1017-1027 (1999)). eIF4E then is free to associate with the rest of the translation initiation complex. OSKAR, 5C and CYC B were identified in a DNA chip screen. CREB, STAU, FAF, MAGO, PUM, ORB and CDC2 were identified from an independent behavioral screen for memory mutants.

DETAILED DESCRIPTION OF THE INVENTION

In various species, long-term memory (LTM) is defined by two main biological properties. First, formation of long-term memory requires synthesis of new proteins. Second, it involves cAMP-responsive transcription and is mediated through the cAMP-response element binding protein (CREB) family transcription factors. Thus, numerous early studies demonstrated that infusions of protein synthesis inhibitors and RNA synthesis inhibitors around the time of training, blocks long-term memory but not short-term memory. A compelling role for CREB as a molecular switch for long-term memory emerged from an analysis of recent "loss- and gain-of-function" experiments in *Drosophila,* Aplysia, mice and rats. Specifically, blocking CREB function has no effect on initial learning or early memory, but long-term memory does not form. Enhancing CREB function causes long term memory to form with less training (practice)—the functional equivalent of a photographic memory.

In vertebrates, CREB is expressed widely in the brain and appears involved in various aspects of developmental and behavioral plasticity (both implicit and explicit forms of memory). These observations suggest, more generally, that pharmacological enhancers of the CREB pathway will reduce the requirement for repetitive "training sessions" to achieve performance gains from cognitive training, while inhibition of CREB pathway, will reduce memory.

Based on cellular studies of CREB function in neurons, a "weak versus strong" contextual fear conditioning protocol was developed that would be sensitive to "upstream" modulation of the CREB pathway (Kaang, B. K. et al., *Neuron,* 10(3):427-435 (1993)). During acquisition, repeated training trials lead to increases in cAMP levels and activation of protein kinase A (PKA). After surpassing a threshold level, activated PKA (catalytic subunit) is translocated to the nucleus, where it phosphorylates CREB (or it yields a permissive state for the phosphorylation of CREB by a cofactor). Phosphorylated CREB induces the transcription of genes encoding proteins required for long-lasting plasticity and memory. In this context:

i) Phosphodiesterase inhibitors (PDEI) would act to increase cAMP levels beyond the threshold in fewer training trials, thereby producing optimal long-term memory with "weaker" (less) training.

ii) Disruption of CREB expression would reduce long-term memory induced by "strong" training to the levels produced by "weak" training.

iii) Long-term memory for contextual fear conditioning would be sensitive to inhibitors of protein synthesis administered around the time of training.

iv) Neuronal genes working in "orchestrated" manner with CREB pathway would be involved in learning and/or memory.

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior (Fanselow, M. S., *Behav. Neurosci.,* 98:269-277 (1984); Fanselow, M. S., *Behav. Neurosci.,* 98:79-95 (1984); and Phillips, R. G. and LeDoux, J. E., *Behav. Neurosci.,* 106:274-285 (1992)). Contextual conditioning has been used to investigate the neural substrates mediating fear-motivated learning (Phillips, R. G. and LeDoux, J. E., *Behav. Neurosci.,* 106:274-285 (1992); and Kim, J. J. et al., *Behav. Neurosci.,* 107:1093-1098 (1993)). Recent studies in mice and rats provided evidence for functional interaction between hippocampal and nonhippocampal systems during contextual conditioning training (Maren, S. et al., *Behav. Brain Res.,* 88(2):261-274 (1997); Maren, S. et al., *Neurobiol. Learn. Mem.,* 67(2):142-149 (1997); and Frankland, P. W. et al., *Behav. Neurosci.,* 112: 863-874 (1998)). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory (Bourtchouladze et al., *Cell,* 79:59-68 (1994); Bourtchouladze et al., *Learn Mem.,* 5(4-5):365-374 (1998); Kogan, J. H. et al., *Current Biology,* 7(1): 1-11 (1997); Silva A. J. et al., *Current Biology,* 6(11): 1509-1518 (1996); Abel, T. et al., *Cell,* 88:615-626 (1997); and Giese, K. P. et al., *Science,* 279:870-873 (1998)) and strain differences in mice (Logue, S. F. et al., *Neuroscience,* 80(4):1075-1086 (1997); Chen, C. et al., *Behav. Neurosci.,* 110:1177-1180 (1996); and Nguyen, P. V. et al., *Learn Mem.,* 7(3):170-179 (2000)). Because robust learning can be triggered with a few minutes training session, contextual conditioning has been especially useful to study the biology of temporally distinct processes of short- and long-term memory (Kim, J. J. et al., *Behav. Neurosci.,* 107:1093-1098 (1993); Abel, T. et al., *Cell,* 88:615-626 (1997); Bourtchouladze et al., *Cell,* 79:59-68 (1994); Bourtchouladze et al., *Learn Mem.,* 5(4-5):365-374 (1998)). As such, contextual conditioning provides an excellent model to evaluate the role of various novel genes in hippocampal-dependent memory formation.

One such gene is a gene encoding a STAUFEN protein. STAUFEN is a critical protein for the targeting of specific mRNAs in *Drosophila* during development (Li, P. et al., *Cell,* 90:437-447 (1997); and Ephrussi, A. and Lehmann, R., *Nature,* 358:387-392 (1992)). Recently, it was shown to be present in the adult rat brain as well. Specifically, STAUFEN was detected in somata and dendrites of neurons of the adult rat hippocampus and cerebral cortex (Monshausenm M. et al., *J. Neurochem.,* 76:155-165 (2001)). In hippocampal neurons, STAUFEN accumulates along microtubules and is thought to participate in the trafficking of mRNA (Tang, S. J. et al., *Neuron*, 32(3):463-475 (2001)).

Recent studies in *Drosophila* identified STAUFEN as a candidate memory gene (CMG) expressed at a high level after long term memory formation. Moreover, temporary disruption of STAUFEN function in temperature-sensitive $stau^{C8}/stau^{D3}$ mutant flies, almost completely abolished 24 hour memory, indicating an acute requirement for STAUFEN during memory consolidation.

Applicants have discovered that STAUFEN plays an important role in mediating the cellular events underlying memory formation in mammals. As described herein, to examine the functional connection of hippocampal STAUFEN to contextual long-term memory formation, hippocampal infusions of antisense oligonucleotides (ODNs) directed against Staufen mRNA were performed. To validate the sensitivity of a "weak versus strong" training-induced memory on CREB-dependent transcription and protein synthesis, a combined behavioral, pharmacological and ODN approach was used.

Five training trials (5×"strong" training) was found to induce maximal levels of long term contextual memory, which is significantly stronger than memory induced by two training trials (2×"weak" training). By injecting the CREB antisense oligonucleotides into the hippocampus before training, a reduction of memory induced by strong training to the levels produced by weak training was observed. Similarly, injection of staufen antisense oligonucleotides into the hippocampus reduced memory induced by strong training. In contrast, Rolipram, a type-IV phosphodiesterase inhibitor, administered immediately after training, enhances the amount of memory induced by weak training to the levels produced by strong training. Finally, an inhibitor of protein synthesis, anisomycin (ANI), blocks both weak- and strong training-induced contextual memory.

Combined, these studies underscore the parallel dependence of long-term contextual memory induced by strong training on protein synthesis and CREB-dependent transcription and they implicate the involvement of hippocampal STAUFEN in contextual memory formation.

mRNAs are present in neuronal dendrites and may be used for local protein synthesis in response to synaptic activity (Steward, O. and Levy, W. B., *J. Neurosci.*, 2:284-291 (1982); and Schuman, E. M., *Neuron*, 23:645-648 (1999)). Recent studies have demonstrated that dendritic protein synthesis can accompany plasticity and participate in long-lasting synaptic changes (Wu, L. et al., *Neuron*, 21:1129-1139 (1998); Huber, K. M. et al., *Science*, 288:1254-1257 (2000); and Casadio, A. et al., *Cell*, 99:221-237 (1999)).

STAUFEN already has been implicated in mRNA localization in mammalian neurons. In hippocampal neurons, STAUFEN has a punctate, somato-dendritic distribution and is a component of large RNP-containing neural granules, which themselves are associated with microtubules (Steward, O. and Schuman, E. M., *Annu. Rev. Neurosci.*, 24:299-325 (2001); Krichevsky, A. M. and Kosik, K. S., *Neuron*, 32:683-696 (2001); Tang, S. J. et al., *Neuron*, 32:463-475 (2001); Kiebler, M. A. et al., *J. Neurosci.*, 19:288-297 (1999); Kohrmann, M. et al., *Mol. Biol. Cell.*, 10: 2945-2953 (1999); and Aakalu, G. et al., *Neuron*, 30:489-502 (2001)). These neural granules appear to play an analogous role in targeting mRNA translation to subcellular (synaptic) compartments in neurons, as do polar granules in *Drosophila* oocytes (Steward, O. and Schuman, E. M., *Annu. Rev. Neurosci.*, 24:299-325 (2001); Johnstone, O. and Lasko, P., *Anni. Rev. Genet.*, 35:3654406 (2001); Palacios, I. M. and Johnston, D. S., *Annu. Rev. Cell. Dev. Biol.*, 17:569-614 (2001); Tang, S. J. et al., *Proc. Natl. Acad. Sci. USA*, 99:467-472 (2002); Aakalu, G. et al., *Neuron*, 30:489-502 (2001); Crino, P. B. and Eberwine, J., *Neuron*, 17:1173-1187 (1996); and Torre, E. R. and Steward, O., *J. Neurosci.*, 12:762-772 (1992)). In cultured hippocampal neurons, neural granules are located near dendritic spines and appear to dissociate in response to local synaptic activity, thereby releasing translationally repressed mRNAs. This process has been proposed as a mechanism for synapse-specific modification via local protein synthesis in response to neural activity (Steward, O. and Schuman, E. M., *Annu. Rev. Neurosci.*, 24:299-325 (2001)). The occurrence in dendrites of protein synthesis and the presence there of the cellular machinery for translation are firmly established (Tang, S. J. et al., *Proc. Natl. Acad. Sci. USA*, 99:467-472 (2002); Aakalu, G. et al., *Neuron*, 30:489-502 (2001); Crino, P. B. and Eberwine, J., *Neuron*, 17:1173-1187 (1996); and Torre, E. R. and Steward, O., *J. Neurosci.*, 12:762-772 (1992)). The findings described herein imply that these cellular processes are engaged during long term memory formation and, more generally, that the similarity between polar granules in the oocyte and neural granules in neurons is not limited to STAUFEN protein. Thus, the mechanistic relations among many CMGs likely will be similar in neurons as occur for trafficked genes in oocytes. By analogy to what is known about local translational control in embryos, it is reasonable to expect that additional components of neural granules that are suggested as CMGs from DNA chip experiments or as memory mutants from complementary behavioral experiments also will be involved in this neuronal process underlying long-term memory formation.

DNA chip experiments on wildtype *Drosophila* and behavioral screens for memory mutants in *Drosophila* have identified fat facets (faf), mago nashi (mago), pumilio (pum), orb, cdc2, eIF2G, eIF-5C, oskar (osk) and cyclin B as CMGs, which are known to interact with staufen (stau). The staufen, fat facets, mago nashi, pumilio, orb, cdc2 and eIF2G genes were identified directly from the DNA chip experiments as transcriptionally regulated genes during long term memory formation. The eIF-5C, oskar and cyclin B genes were identified from the behavioral screens for memory mutants (defective in one-day memory after spaced training). Together, these genetic components, staufen (FlyBase #FBgn0003520; vertebrate homologs: gi:4759176 (human), gi:4335945 (mouse)), fat facets (FlyBase #FBgn0005632; vertebrate homologs: gi:4759294 (human), MGI:89468 (mouse)), mago nashi (FlyBase #FBgn0002736; vertebrate homolog: gi:4505087 (human)), pumilio (FlyBase #CG1755; FlyBase #FBgn0003165; vertebrate homolog: gi:1944416 (human)), orb (FlyBase #FBgn0004882; vertebrate homologs: gi:4589524 (human), MGI:108442 (mouse)), cdc2 (FlyBase #FBgn0004106; vertebrate homologs: gi:4502709 (human), MGI:88351 (mouse)), eIF2G (FlyBase #FBgn003600; vertebrate homologs: gi:4503507 (human), gi:3790184 (mouse)), eIF-5C (FlyBase #CG2922; vertebrate homologs: gi:286001 (human), gi:4426565 (rat)), oskar (FlyBase #CG10901) and cyclin B (FlyBase #CG3510; vertebrate homologs: OMIM: 123836 (human), MGI:88298 (mouse)) (Gelbart, W. M., et al., *Nucleic Acids Research*, 25:63-66 (1997); Flybase, http://flybase.bio.indiana.edu/, *Nucleic Acids Research*, 27:85-88 (1999)), define a biological pathway involved with subcellular localization of mRNAs and local regulation of translation, a cellular mechanism that may link CREB-dependent transcription in the nucleus with the tagging of specific synapses underlying long-term memory formation. This pathway is also referred to herein as the "staufen pathway", the "pumilio pathway" or the "pumilio/staufen pathway". The evolutionary conservation of gene function that has been observed repeatedly indicates that many homologs of identified *Drosophila* genes likely subserve similar roles in vertebrate memory formation.

A model for synapse-specific modification underlying long-term memory formation is shown in FIGS. 7A-7B. First, behavioral training results in activation of CREB-mediated transcription and nascent mRNAs are packaged into an RNP complex, a neural granule. These granules likely include genetic components of polar granules such as stau, osk, mago and faf and perhaps additional RNA binding CMGs (RNP-4f, hnRNP-A 1, no-on transient A, PO, GCR101, La). These neural granules then are transported into dendritic shafts along an organized microtubule network (Johnstone, O. and Lasko, P., *Annu. Rev. Genet.*, 35:365-406 (2001); Palacios, I. M. and Johnston, D. S., *Annu. Rev. Cell. Dev. Biol.*, 17:569-614 (2001); Tang, S. J. et al., *Neuron,* 32:463-475 (2001); and Kohrmann, M. et al., *Mol. Biol. Cell.,* 10: 2945-2953 (1999)). Activity-induced transcripts may be delivered to all dendrites or selectively to sites of recent synaptic activity (Barco, A. et al., *Cell,* 108:689-703 (2002); Frey, U. and Morris, R. G., *Nature,* 385:533-536 (1997); Martin, K. C. et al., *Cell,* 91:927-938 (1997); and Steward, O. and Worley, P. F., *Neuron,* 30:227-240 (2001)). In either case, packaged mRNAs likely are translationally quiescent while in transport (Krichevsky, A. M. and Kosik, K. S., *Neuron,* 32:683-696 (2001)), thereby preventing ubiquitous expression. It is reasonable to expect that this translational repression complex includes pum. In this model, synapse-specific modification results from the depolarization-dependent release of neural granule-associated mRNAs and translational derepression at recently active synapses (Krichevsky, A. M. and Kosik, K. S., *Neuron,* 32:683-696 (2001); and Aakalu, G. et al., *Neuron,* 30:489-502 (2001)).

The process of derepression appears to involve phosphorylation of CPEB (orb) by aurora kinase, resulting in cytoplasmic polyadenylation (Richter, J. D., *Proc. Natl. Acad. Sci. USA,* 98:7069-7071 (2001); Wells, D. G. et al., *Curr. Opin. Neurobiol.,* 10:132-137 (2000); Wu, L. et al., *Neuron,* 21:1129-1139 (1998); and Huang, Y. S. et al., *EMBO J.,* 21:2139-2148 (2002)) and the dissociation of MASKIN from eIF4-E, which then allows interaction between eIF4-E with eIF4-G (Stebbins-Boaz, B. et al., *Mol. Cell.,* 4:1017-1027 (1999)). Release of eIF-4E via phosphorylation of other 4E binding proteins also may promote assembly of the rest of the translation initiation complex (Tang, S. J. et al., *Proc. Natl. Acad. Sci. USA,* 99:467-472 (2002)). The presence during synaptic or behavioral plasticity of several persistently active kinases also may contribute to such phosphorylation (Tang, S. J. et al., *Proc. Natl. Acad. Sci. USA,* 99:467-472 (2002); Ling, D. S. et al., *Nat. Neurosci.,* 5:295-296 (2002); Drier, E. A. et al., *Nat. Neurosci.,* 5:316-324 (2002); Selcher, J. C. et al., *Neuroscientist,* 8:122-131 (2002); Chain, D. G. et al., *J. Neurosci.,* 15:7592-7603 (1995); and Muller, U. and Carew, T. J., *Neuron,* 21:1423-1434 (1998)). Finally, CPEB-mediated translational activation in Xenopus oocytes is associated with phosphorylation of ORB by CDC2 kinase (which is a dimer of CycB and CDC2) (Mendez, R. et al., *EMBO J.,* 21:1833-1844 (2002)) and ubiquitin-mediated degradation of ORB (Reverte, C. G. et al., *Dev. Biol.,* 231:447-458 (2001)), perhaps modulated by faf. The DNA chip and memory mutant experiments have identified several potential components (pum, orb, cdc2, CycB, faf, eIF5-C, eIF2-G, and ribosomal protein PO).

The results link two biological phenomena of LTM, transcription dependence and synaptic tagging (Barco, A. et al., *Cell,* 108:689-703 (2002); Casadio, A. et al., *Cell,* 99:221-237 (1999); Frey, U. and Morris, R. G., *Nature,* 385:533-536 (1997); Martin, K. C. et al., *Cell,* 91:927-938 (1997); and Steward, O. et al., *Neuron,* 21:741-751 (1998)), with two well-known cellular mechanisms, mRNA translocation and local, activity-dependent regulation of translation (FIGS. 7A-7B) (Steward, O. and Schuman, E. M., *Annu. Rev. Neurosci.,* 24:299-325 (2001)).

The present invention provides cell-based screening methods for identifying a pharmaceutical agent which is capable of modulating STAUFEN function by screening for STAUFEN function. By "capable of modulating STAUFEN function" is meant to include pharmaceutical agents which can modulate STAUFEN function. In one embodiment, STAUFEN function is screened by determining the level of STAUFEN protein expression (translation). As described herein, STAUFEN is transcriptionally upregulated during memory formation. Accordingly, in this embodiment, STAUFEN protein expression can be determined by determining STAUFEN mRNA or protein production. In a second embodiment, STAUFEN function is screened by determining the functional readout of STAUFEN. In this embodiment, a functional readout of STAUFEN can be determined by detecting (such as using an antibody) the translocation of the STAUFEN into dendrites or by determining the level of STAUFEN protein production. A functional readout of STAUFEN can also be determined indirectly by detecting and measuring downstream gene products regulated by a staufen gene product. In a third embodiment, STAUFEN function is screened by determining the change in distribution of neural granules in the cells.

By "STAUFEN function" is meant the biological activity of STAUFEN, which includes subcellular translocation of various mRNAs and local regulation of various protein translations ("the STAUFEN pathway"). Biological activity is understood to mean biological function or action. By "STAUFEN pathway function" is meant a set of gene products which interact with a staufen gene product and/or with each other to produce STAUFEN function, particularly the subcellular translocation of mRNA and local regulation of protein translation.

In a particular embodiment, STAUFEN::indicator fusion protein constructs are employed in cell-based screening methods for identifying a pharmaceutical agent which is capable of modulating STAUFEN function. Thus, in one embodiment, a cell-based screening method for identifying a pharmaceutical agent which is capable of modulating STAUFEN function comprises (a) introducing a pharmaceutical agent to be evaluated for its ability to modulate STAUFEN function into host cells (particularly cells of neural origin) expressing a STAUFEN::indicator fusion protein (e.g., STAUFEN::GFP fusion protein); and (b) determining STAUFEN function. In a particular embodiment, the pharmaceutical agent is introduced into the cells after stimulation of the CREB pathway using forskolin. By CREB pathway is meant CREB-dependent gene expression. The STAUFEN function determined in step (b) is compared to the STAUFEN function of the host cells of step (a) to which the pharmaceutical agent has not been introduced (untreated host cells expressing STAUFEN::indicator fusion protein) (control). A difference in STAUFEN function of the treated cells relative to the STAUFEN function of the untreated cells identifies the pharmaceutical agent as one which modulates (or is capable of modulating) STAUFEN function.

In one embodiment, STAUFEN function is determined by detecting and determining the level of STAUFEN::indicator fusion protein expression (translation) (e.g., by detecting STAUFEN::indicator fusion protein mRNA or protein production). In a second embodiment, STAUFEN function is determined by detecting (such as using an antibody) the translocation of the STAUFEN::indicator fusion protein into dendrites or by determining the level of STAUFEN::indicator fusion protein production. In a third embodiment, STAUFEN function is determined indirectly by detecting and measuring downstream gene products regulated by a staufen gene product. In a fourth embodiment, STAUFEN function is determined by determining the change in distribution of neural granules in the cells.

In another embodiment, a cell-based screening method for identifying a pharmaceutical agent capable of modulating STAUFEN function comprises (a) introducing a pharmaceutical agent to be evaluated for its ability to modulate STAUFEN function into host cells of neural origin, said cells expressing STAUFEN::indicator fusion protein; and (b) detecting the translocation of the STAUFEN::indicator fusion protein into dendrites. In a particular embodiment, the pharmaceutical agent is introduced into the cells after stimulation of the CREB pathway using forskolin. A difference in translocation of STAUFEN::indicator fusion protein into dendrites in the presence of a pharmaceutical agent relative to its translocation in the absence of pharmaceutical agent identifies the pharmaceutical agent as one which modulates (or is capable of modulating) STAUFEN function.

Cells expressing a STAUFEN::indicator fusion protein can be produced by introducing into host cells a DNA construct comprising (1) DNA encoding a STAUFEN::indicator fusion protein (e.g., STAUFEN::GFP fusion protein); and (2) a promoter sequence of a ubiquitously expressed gene, wherein the promoter sequence is operably linked to the DNA encoding the STAUFEN::indicator fusion protein. In a particular embodiment, the DNA construct is introduced into host cells, e.g., via a vector, which causes the fusion protein to be expressed in the cells. Expression of the STAUFEN::indicator fusion protein can be transient or stable. As used herein, "a promoter sequence of a ubiquitously expressed gene" refers to a promoter sequence of a gene with widespread expression. Examples of ubiquitously expressed genes are known in the art and include the actin gene and the ELAV gene.

A vector, as the term is used herein, refers to a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, 3rd Edition, B. N. Fields, et al., eds., Philadelphia, Pa.; Lippincott-Raven Publishers) (1996)). Other examples include Sindbis virus, murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

DNA encoding a STAUFEN::indicator fusion protein can be manufactured as described using methods known and described in the art (see, e.g., Ausubel et al., *Current Protocols In Molecular Biology* (New York: John Wiley & Sons) (1998); and Sambrook et al., *Molecular Cloning: A Laboratory Manual,* 2nd edition (New York: Cold Spring Harbor University Press (1989)). DNA constructs comprising a promoter sequence operably linked to DNA encoding a STAUFEN::indicator fusion protein can be manufactured as described using methods known and described in the art (see, e.g, Ausubel et al., *Current Protocols In Molecular Biology* (New York: John Wiley & Sons) (1998); and Sambrook et al., *Molecular Cloning: A Laboratory Manual,* 2nd edition (New York: Cold Spring Harbor University Press (1989)). DNA constructs can be introduced into cells according to methods known in the art (e.g., transformation, direct uptake, calcium phosphate precipitation, electroporation, projectile bombardment, using liposomes). Such methods are described in more detail, for example, in Sambrook et al, *Molecular Cloning: A Laboratory Manual,* 2nd edition (New York: Cold Spring Harbor University Press) (1989); and Ausubel, et al., *Current Protocols in Molecular Biology* (New York: John Wiley & Sons) (1998).

A vector, as the term is used herein, refers to a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology,* 3rd Edition, B. N. Fields, et al., eds., Philadelphia, Pa.: Lippincott-Raven Publishers) (1996)). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Anti-staufen antibodies can also be used to determine whether a particular pharmaceutical agent has an effect on STAUFEN function, such as by detecting translocation of STAUFEN protein, as described above. Anti-staufen antibodies can also be used to determine whether a particular pharmaceutical agent has an effect on the levels of STAUFEN protein expression (translation) by detecting STAUFEN protein production.

The present invention also encompasses methods of screening for or identifying a pharmaceutical agent which is capable of modulating STAUFEN function comprising (a)

introducing into host cells (particularly cells of neural origin) a DNA construct, wherein the DNA construct comprises (1) DNA encoding an indicator gene; and (2) a staufen promoter sequence operably linked to the DNA encoding the indicator gene; (b) producing a sample by introducing into host cells comprising the DNA construct a pharmaceutical agent to be assessed for its ability to modulate STAUFEN function under conditions appropriate for expression of the indicator gene; (c) detecting and determining the level of indicator gene product produced in the sample obtained in step (b); and (d) comparing the level of indicator gene product detected in step (c) with the level of indicator gene product detected in control cells into which the pharmaceutical agent has not been introduced. A difference in the level of indicator gene product in the sample obtained in step (b) compared to the level of indicator gene product in control cells identifies the pharmaceutical agent as one which modulates STAUFEN function. By "staufen promoter sequence" is meant a promoter sequence usually upstream (5') of the coding region of the staufen gene, which controls the expression of the coding region by providing recognition and binding sites for RNA polymerase and other factors which may be required for initiation of transcription.

DNA constructs comprising a promoter sequence operably linked to DNA encoding an indicator gene can be manufactured as described using methods known and described in the art. See, for example, Ausubel et al., *Current Protocols In Molecular Biology* (New York: John Wiley & Sons) (1998); and Sambrook et al., *Molecular Cloning: A Laboratory Manual,* 2nd edition (New York: Cold Spring Harbor University Press (1989).

The term "indicator gene", as used herein, refers to a nucleic acid sequence whose product can be easily assayed, for example, calorimetrically as an enzymatic reaction product, such as the lacZ gene which encodes β-galactosidase. Other examples of widely used indicator genes include those encoding enzymes, such as β-glucoronidase and β-glucosidase; luminescent molecules, such as green fluorescent protein (GFP) and firefly luciferase; and auxotrophic markers such, as His3p and Ura3p. See, e.g., Ausubel et al., *Current Protocols In Molecular Biology* (New York: John Wiley & Sons, Inc.), Chapter 9 (1998)).

As used herein, a cell refers to an animal cell. The cell can be a stem cell or somatic cell. Suitable animal cells can be of, for example, mammalian origin. Examples of mammalian cells include human (such as HeLa cells), bovine, ovine, porcine, murine (such as embryonic stem cells), rabbit and monkey (such as COS1 cells) cells. Preferably, the cell is of neural origin (such as a neuroblastoma, neuron, neural stem cell, etc.). The cell can also be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The cells can be obtained commercially or from a depository or obtained directly from an animal, such as by biopsy.

The pharmaceutical agent can be introduced into host cells (particularly cells of neural origin) either alone or after stimulation of the CREB pathway using forskolin.

Pharmaceutical agents which modulate, or are capable of modulating, STAUFEN function are further screened to determine the effect of the agents on long term memory formation or to identify those agents capable of modulating long term memory. In one embodiment, the method comprises (a) administering to an animal (particularly a mammal) a pharmaceutical agent which modulates, or is capable of modulating, STAUFEN function; (b) training the animal of (a) and a control animal of the same species to which the pharmaceutical agent has not been administered under conditions sufficient to produce long term memory formation in the animals; (c) assessing long term memory formation in the animals trained in step (b); and (d) comparing long term memory formation in the animals assessed in step (c). A control animal is the basis for comparison in assessing results associated with administration of a pharmaceutical agent to an experimental animal. The experimental and control animals are comparable, e.g., same age, genetic makeup, basal STAUFEN function (i.e., STAUFEN function prior to treatment with the pharmaceutical agent). A difference in long term memory formation assessed in the animal treated with (administered) the pharmaceutical agent relative to the long term memory formation assessed in the control animal identifies the pharmaceutical agent as one which has the ability to modulate long term memory formation in the animal.

Pharmaceutical agents which modulate, or are capable of modulating, STAUFEN function are also screened to determine the effect of the agents on performance by an animal of a hippocampal-dependent cognitive task or to identify those agents capable of modulating performance of a hippocampal-dependent cognitive task by an animal. In one embodiment, the method comprises (a) administering to an animal (particularly a mammal) a pharmaceutical agent which modulates, or is capable of modulating, STAUFEN function; (b) training the animal of (a) and a control animal of the same species to which the pharmaceutical agent has not been administered under conditions appropriate for performance by the animals of a specified hippocampal-dependent cognitive task; (c) assessing performance of the hippocampal-dependent cognitive task by the animals trained in step (b); and (d) comparing performance of the animals assessed in step (c). The experimental and control animals are comparable, e.g., same age, genetic makeup, basal STAUFEN function (i.e., STAUFEN function prior to treatment with the pharmaceutical agent). A difference in assessed performance by the animal treated with (administered) the pharmaceutical agent relative to the assessed performance by the control animal identifies the pharmaceutical agent as one which has the ability to modulate the performance by the animal of the specified hippocampal-dependent cognitive task.

The present invention also provides methods for screening a pharmaceutical agent for its ability to modulate long term memory formation in an animal and for assessing its effect on long term memory in an animal. Preferably, the animal is an adult mammal. In one embodiment, the method comprises (a) administering to a first animal a pharmaceutical agent of interest; (b) determining STAUFEN function in the animal administered the pharmaceutical agent in (a) relative to STAUFEN function in a control animal of the same species as the first animal to which the pharmaceutical agent has not been administered; (c) selecting the pharmaceutical agent if the STAUFEN function determined in (b) differs from the STAUFEN function in the control animal; (d) administering the pharmaceutical agent selected in (c) to a second animal; (e) training the second animal administered the pharmaceutical agent in (d) and a control animal of the same species as the second animal under conditions appropriate to produce long term memory formation in the animals; (f) assessing long term memory formation in the animals trained in step (e); and (g) comparing long term memory formation in the animals assessed in step (f). The first and second animals can be of the same or different species. The first animal and the corresponding control animal are comparable, e.g., same age, genetic makeup, basal STAUFEN function (i.e., STAUFEN function prior to treatment with the pharmaceutical agent). Similarly, the second animal and the corresponding control animal are comparable, e.g., same age, genetic makeup, basal STAUFEN function (i.e., STAUFEN function prior to treatment with (administration of) the pharmaceutical agent). A difference in long term memory formation assessed in the animal treated with the pharmaceutical agent relative to the long term memory formation assessed in the control animal identifies the pharmaceutical agent as one which has the ability to modulate long term memory formation in the animal.

The present invention also encompasses methods for screening a pharmaceutical agent for its ability to modulate STAUFEN function in an animal and for assessing the effect of a pharmaceutical agent on STAUFEN function in an animal. Preferably, the animal is an adult mammal. In one embodiment, the method comprises (a) administering a pharmaceutical agent of interest to the animal; and (b) determining STAUFEN function in the animal obtained in (a) relative to STAUFEN function in a control animal of the same species to which the pharmaceutical agent has not been administered. The experimental and control animals are comparable, e.g., same age, genetic makeup, basal STAUFEN function (i.e., STAUFEN function prior to treatment with the pharmaceutical agent). A difference in STAUFEN function determined in the animal treated with the pharmaceutical agent relative to STAUFEN function determined in the control animal identifies the pharmaceutical agent as one having the ability to modulate STAUFEN function in the animal.

The invention also relates to methods for screening a pharmaceutical agent for its ability to modulate performance of a hippocampal-dependent cognitive task by an animal and for assessing the effect a pharmaceutical agent on performance of a hippocampal-dependent cognitive task by an animal. In a particular embodiment, the animal is an adult mammal. In one embodiment, the method comprises (a) administering a pharmaceutical agent of interest to a first animal; (b) determining STAUFEN function in the animal administered the pharmaceutical agent in (a) relative to STAUFEN function in a control animal of the same species to which the pharmaceutical agent has not been administered; (c) selecting the pharmaceutical agent if the STAUFEN function determined in (b) differs from the STAUFEN function in the control animal; (d) administering the pharmaceutical agent selected in (c) to a second animal; (e) training the animal administered the pharmaceutical agent in (d) and a control animal of the same species as the second animal under conditions appropriate for performance by the animals of a specified hippocampal-dependent cognitive task; (f) assessing performance of the hippocampal-dependent cognitive task by the animals trained in step (e); and (g) comparing performance of the animals assessed in step (f). The first and second animals can be of the same or different species. The first animal and the corresponding control animal are comparable, e.g., same age, genetic makeup, basal STAUFEN function (i.e., STAUFEN function prior to treatment with the pharmaceutical agent). Similarly, the second animal and the corresponding control animal are comparable, e.g., same age, genetic makeup, basal STAUFEN function (i.e., STAUFEN function prior to treatment with the pharmaceutical agent). A difference in assessed performance by the animal treated with the pharmaceutical agent relative to the assessed performance by the control animal identifies the pharmaceutical agent as one which has the ability to modulate the performance by the animal of the specified hippocampal-dependent cognitive task.

As used herein, training can comprise one or multiple training sessions and is training appropriate for long term memory formation or for performance of the specified cognitive task. The pharmaceutical agent can be administered before, during or after one or more of the training sessions. By "training" is meant cognitive training.

Training of mammals for long term memory formation is conducted using methods generally known in the art (see, e.g., Josselyn et al., Society for Neurosci., 24:926, Abstract 365.10 (1998); Guzowski et al., Proc. Natl. Acad. Sci. USA, 94:2693-2698 (1997); Lamprecht et al., J. Neuroscience, 17(21):8443-8450 (1997): Bourtchuladze et al., Cell, 79:59-68 (1994); and Kogan et al., Curr. Biol., 7:1-11 (1996)). Training of mammals for performance of specified hippocampal-dependent cognitive tasks is conducted using methods generally known in the art (see, e.g., Barnes, C. A. et al, In Brain and Memory: Modulation and Mediation of Neuroplasticity, J. L. McGaugh et al. (Eds.), Oxford University Press, pp. 259-276 (1995); Jarrard, L. E., Behavioral Neural Biology, 60:9-26 (1993); Moser, M. B. et al., Proc. Natl. Acad. Sci. USA, 92(21):9697-9701 (1995); Chen, C. et al., Behav. Neurosci., 110:1177-1180 (1996); Frankland, P. W. et al., Behav. Neurosci., 112:863-874 (1998); Holland, P. C. and Bouton, M. E., Curr. Opin. Neurobiol., 9:195-202 (1999); Kim, J. J. et al., Behav. Neurosci., 107:1093-1098 (1993); Logue, S. F. et al., Behav. Neurosci., 111: 104-113 (1997); and Squire, L. R., Psychological Review, 99:195-231 (1992)).

Pharmaceutical agents (drugs), as used herein, are compounds with pharmacological activity and include inorganic compounds, ionic materials, organic compounds, organic ligands, including cofactors, saccharides, recombinant and synthetic peptides, proteins, peptoids, nucleic acid sequences, including genes, nucleic acid products.

Pharmaceutical agents can be individually screened. Alternatively, more than one pharmaceutical agent can be tested simultaneously for the ability to modulate long term memory formation and/or the ability to modulate performance of a hippocampal-dependent cognitive task and/or the ability to modulate STAUFEN function in accordance with the methods herein. Where a mixture of pharmaceutical agents is tested, the pharmaceutical agents selected by the methods described can be separated (as appropriate) and identified by suitable methods (e.g., chromatography, sequencing, PCR).

Large combinatorial libraries of pharmaceutical agents (e.g., organic compounds, recombinant or synthetic peptides, peptoids, nucleic acids) produced by combinatorial chemical synthesis or other methods can be tested (see e.g., Zuckerman, R. N. et al., J. Med. Chem., 37:2678-2685 (1994) and references cited therein; see also, Ohlmeyer, M. H. J. et al., Proc. Nat. Acad. Sci. USA, 90:10922-10926 (1993) and DeWitt, S. H. et al., Proc. Natl. Acad. Sci. USA, 90:6909-6913 (1993), relating to tagged compounds; Rutter, W. J. et al., U.S. Pat. No. 5,010,175; Huebner, V. D. et al., U.S. Pat. No. 5,182, 366; and Geysen, H. M., U.S. Pat. No. 4,833,092). The teachings of these references are incorporated herein by reference. Where pharmaceutical agents selected from a combinatorial library carry unique tags, identification of individual pharmaceutical agents by chromatographic methods is possible.

Chemical libraries, microbial broths and phage display libraries can also be tested (screened) for the presence of one or more pharmaceutical agent(s) which are capable of modulating long term memory formation and/or modulating performance of a hippocampal-dependent cognitive task and/or modulating STAUFEN function in accordance with the methods herein.

Pharmaceutical agents identified in accordance with the screening methods herein can be administered to an animal to modulate or enhance long term memory formation or performance of a hippocampal-dependent cognitive task in accordance with the methods herein. Pharmaceutical agents identified in accordance with the screening methods herein can also be administered in the treatment of the animal with a defect in long term memory formation that is associated with a defect in STAUFEN or an animal with a defect in performance of a hippocampal-dependent cognitive task, wherein the defect is associated with a defect in STAUFEN, in accordance with the methods herein.

As used herein, a defect in long term memory formation associated with a defect in STAUFEN can be a biochemical or developmental defect. The defect in STAUFEN is either a diminution in the amount of STAUFEN produced, a diminution in STAUFEN function of STAUFEN produced or both a diminution in amount of STAUFEN produced and a diminution in STAUFEN function.

"Modulating", as the term is used herein, includes induction, enhancement, potentiation, reduction, blocking, inhibition (total or partial) and regulation. By "regulation", as the term is used herein, is meant the ability to control the rate and extent to which a process occurs.

By "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal. As a result, long term memory acquisition is faster or better retained. Enhancing performance of a hippocampal-dependent cognitive task refers to the ability to potentiate or improve performance of a specified hippocampal-dependent cognitive task by an animal relative to the normal performance of the hippocampal-dependent cognitive task by the animal. The term "hippocampal-dependent cognitive task" refers to a cognitive task associated with the hippocampal region of the brain.

In mammals, the hippocampus is essential for the initial consolidation of explicit, or declarative memory. For reviews, see Squire, L. R., *Psychological Review*, 99:195-231 (1992); and Milner, B. et al., *Neuron*, 20:445-468 (1998). In particular, various studies have suggested that the hippocampus plays a key role in spatial memory, such as Morris water maze, Barnes circular maze, radial-arm maze, T-maze and Y-maze (O'Keefe, J. and Nadel, L., *The Hippocampus As A Cognitive Map*, Oxford University Press (1978); Morris, R. G. M. et al., *Nature*, 297:681-683 (1992); Jarrard, L. E., *Behavioral Neural Biology*, 60:9-26 (1993); Moser, M. B. et al., *Proc. Natl. Acad. Sci. USA*, 92(21):9697-9701 (1995); O'Keefe, J., *Hippocampus*, 9:352-364 (1999); Burgess, N. et al., *Biological Cybernetics*, 83:301-312 (2000); and Barnes, C. A. et al., In Brain and Memory: Modulation and Mediation of Neuroplasticity, J. L. McGaugh et al. (Eds.), Oxford University Press, pp. 259-276 (1995)), contextual conditioning (Phillips, R. G. and LeDoux, J. E., *Behav. Neurosci.*, 106:274-285 (1992); Kim, J. J. et al., *Behav. Neurosci.*, 107:1093-1098 (1993); Logue, S. F. et al., *Behav. Neurosci.*, 111:104-113 (1997); Chen, C. et al., *Behav. Neurosci.*, 110: 1177-1180 (1996); and Holland, P. C. and Bouton, M. E., *Curr. Opin. Neurobiol.*, 9:195-202 (1999)), context discrimination (Frankland, P. W. et al., *Behav. Neurosci.*, 112:863-874 (1998); McDonald, R. J. and White, N. M., *Behav. Neurosci.*, 109:579-593 (1995); and McDonald, R. J. and White, N. M., *Hippocampus*, 5(3): 189-197 (1995)) and trace conditioning (Kim, J. J. et al., *Behav. Neurosci.*, 109:195-203 (1995); Buchel, C. et al., *J. Neurosci.*, 19(24):10869-10876 (1999); Clark, R. E. and Squire, L. R., *Science*, 280:77-81 (1998); McGlinchey-Berroth, R. et al., *Behav. Neurosci.*, 111(5):873-882 (1997); and McEchon, M. D. et al., *J. Neurophysiol.*, 86(4):1839-1857 (1998)).

STAUFEN can be an intact protein or a functional or biologically active equivalent of intact STAUFEN protein. A functional or biologically active equivalent of intact STAUFEN protein refers to a molecule which functionally resembles (mimics) intact STAUFEN protein. A functional or biologically active equivalent of intact STAUFEN protein need not have an amino acid sequence analogous to the amino acid sequences of the staufen gene products described herein. For example, a functional equivalent of intact STAUFEN protein can contain a "SLENT" codon or one or more conservative amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., Eds., *Current Protocols In Molecular Biology* (New York: John Wiley & Sons) (1997).

As used herein, the term "animal" includes mammals, as well as other animals, vertebrate and invertebrate (e.g., birds, fish, reptiles, insects (e.g., *Drosophila* species), mollusks (e.g., Aplysia). Preferably, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and primates (e.g., monkeys, chimpanzees), rodents (e.g., rats, mice, guinea pigs) and ruminants (e.g., cows, pigs, horses). The animal is preferably an adult animal.

The invention also relates to methods of modulating long term memory formation in an animal. In a particular embodiment, the animal is an adult mammal. In one embodiment, the method comprises treating the animal to modulate staufen-dependent protein expression. In a second embodiment, the method comprises treating the animal to modulate STAUFEN function. In a particular embodiment, the method comprises administering to the animal an effective amount of a pharmaceutical agent which modulates STAUFEN function in the animal. In another embodiment, the method comprises treating the animal to modulate STAUFEN protein expression. In a particular embodiment, the method comprises administering to the animal an effective amount of a pharmaceutical agent which modulates STAUFEN protein expression in the animal.

The present invention also relates to methods of enhancing long term memory formation in an animal, preferably an adult mammal. In one embodiment, the method comprises treating the animal to modulate staufen-dependent protein expression. In a second embodiment, the method comprises treating the animal to increase STAUFEN function relative to the STAUFEN function in the animal prior to treatment. In a particular embodiment, treatment to increase STAUFEN function comprises administering to the animal an effective amount of a pharmaceutical agent which increases STAUFEN function relative to STAUFEN function in the animal prior to administration of the pharmaceutical agent. In a second embodiment, the method comprises treating the animal to increase STAUFEN protein expression relative to STAUFEN protein expression in the animal prior to treatment. In a particular embodiment, treatment to increase STAUFEN protein expression comprises administering to the animal an effective amount of a pharmaceutical agent which increases STAUFEN protein expression relative to STAUFEN protein expression in the animal prior to administration of the pharmaceutical agent. In another embodiment, the method comprises administering to the animal an effective amount of a STAUFEN molecule, STAUFEN analog, biologically active STAUFEN fragment or STAUFEN fusion protein. In still another embodiment, the method comprises administering to the animal an effective amount of a nucleic acid sequence encoding a STAUFEN molecule, STAUFEN analog, biologically active STAUFEN fragment or STAUFEN fusion protein.

The present invention further provides methods for treating an animal with a defect in long term memory formation associated with a defect in STAUFEN. The animal is preferably an adult mammal. The defect in STAUFEN is either a diminution in the amount of STAUFEN produced, a diminution in STAUFEN function of STAUFEN produced or both a diminution in amount of STAUFEN produced and STAUFEN function of STAUFEN produced. In one embodiment, the method comprises treating an animal with a defect in long term memory formation associated with a defect in STAUFEN to increase STAUFEN function relative to the STAUFEN function in the animal prior to treatment. In a particular embodiment, treatment to increase STAUFEN function comprises administering to the animal an effective amount of a pharmaceutical agent which increases STAUFEN function relative to STAUFEN function in the animal prior to administration of the pharmaceutical agent. In a second embodiment, the method comprises treating an animal with a defect in long term memory formation associated with a defect in STAUFEN to increase STAUFEN protein expression relative to STAUFEN protein expression in the animal prior to treatment. In a particular embodiment, treatment to increase STAUFEN protein expression comprises administering to the animal an effective amount of a pharmaceutical agent which increases STAUFEN protein expression relative to STAUFEN protein expression in the animal prior to administration of the pharmaceutical agent. In a another embodiment, the method comprises administering to an animal with a defect in long term memory formation associated with a defect in STAUFEN a STAUFEN compound such as exogenous STAUFEN, STAUFEN analog, biologically active STAUFEN fragment or STAUFEN fusion protein. In another embodiment, the method comprises administering to an animal with a defect in long term memory formation with a defect in STAUFEN a nucleic acid sequence encoding STAUFEN, STAUFEN analog, biologically active STAUFEN fragment or STAUFEN fusion protein.

The invention also relates to methods of modulating performance of a hippocampal-dependent cognitive task by an animal, preferably an adult mammal. In one embodiment, the method comprises treating the animal to modulate staufen-dependent protein expression. In a second embodiment, the method comprises treating the animal to modulate STAUFEN function. In a particular embodiment, the method comprises administering to the animal an effective amount of a pharmaceutical agent which modulates STAUFEN function in the animal. In another embodiment, the method comprises treating the animal to modulate STAUFEN protein expression. In a particular embodiment, the method comprises administering to the animal an effective amount of a pharmaceutical agent which modulates STAUFEN protein expression in the animal.

The present invention also relates to methods of enhancing performance of a hippocampal-dependent cognitive task by an animal, preferably an adult mammal. In one embodiment, the method comprises treating the animal to modulate staufen-dependent protein expression. In a second embodiment, the method comprises treating the animal to increase STAUFEN function relative to STAUFEN function in the animal prior to treatment. In a particular embodiment, treatment to increase STAUFEN function comprises administering to the animal an effective amount of a pharmaceutical agent which increases STAUFEN function relative to STAUFEN function in the animal prior to administration of the pharmaceutical agent. In another embodiment, the method comprises treating the animal to increase STAUFEN protein expression relative to STAUFEN protein expression in the animal prior to treatment. In a particular embodiment, treatment to increase STAUFEN protein expression comprises administering to the animal an effective amount of a pharmaceutical agent which increases STAUFEN protein expression relative to STAUFEN protein expression in the animal prior to administration of the pharmaceutical agent. In another embodiment, the method comprises administering to the animal an effective amount of STAUFEN, STAUFEN analog, biologically active STAUFEN fragment or STAUFEN fusion protein. In another embodiment, the method comprises administering to the animal an effective amount of a nucleic acid sequence encoding STAUFEN, STAUFEN analog, biologically active STAUFEN fragment or STAUFEN fusion protein.

The present invention further provides methods for treating an animal with a defect in performance of a hippocampal-dependent cognitive task, wherein the defect in performance is associated with a defect in STAUFEN. The animal is preferably an adult mammal. The defect in STAUFEN is either a diminution in the amount of STAUFEN produced, a diminution in STAUFEN function of STAUFEN produced or both a diminution in amount of STAUFEN produced and STAUFEN function of STAUFEN produced. In one embodiment, the method comprises treating an animal with a defect in performance of a hippocampal-dependent cognitive task associated with a defect in STAUFEN to increase STAUFEN function relative to STAUFEN function in the animal prior to treatment. In a particular embodiment, treatment to increase STAUFEN function comprises administering to the animal an effective amount of a pharmaceutical agent which increases STAUFEN function relative to STAUFEN function in the animal prior to administration of the pharmaceutical agent. In a second embodiment, the method comprises treating an animal with a defect in performance of a hippocampal-dependent cognitive task associated with a defect in STAUFEN to increase STAUFEN protein expression relative to STAUFEN protein expression in the animal prior to treatment. In a particular embodiment, treatment to increase STAUFEN protein expression comprises administering to the animal an effective amount of a pharmaceutical agent which increases STAUFEN protein expression relative to STAUFEN protein expression in the animal prior to administration of the pharmaceutical agent. In another embodiment, the method comprises administering to an animal with a defect in performance of a hippocampal-dependent cognitive task associated with a defect in STAUFEN a STAUFEN compound such as exogenous STAUFEN, STAUFEN analog, biologically active STAUFEN fragment or STAUFEN fusion protein. In another embodiment, the method comprises administering to an animal with a defect in performance of a hippocampal-dependent cognitive task associated with a defect in STAUFEN a nucleic acid sequence encoding STAUFEN, STAUFEN analog, biologically active STAUFEN fragment or STAUFEN fusion protein.

The invention also relates to methods for modulating performance by an animal, preferably an adult mammal, of cognitive tasks associated with non-hippocampal regions of the brain where staufen gene expression is found to occur, methods for treating a defect in performance by an animal of cognitive tasks associated with non-hippocampal regions of the brain where staufen gene expression is found to occur and methods for screening a pharmaceutical agent for its ability to modulate performance by an animal of cognitive tasks associated with non-hippocampal regions of the brain where staufen gene expression is found to occur. Such methods are similar to the methods described herein for modulating performance by an animal of hippocampal-dependent cognitive tasks, for treating a defect in performance by an animal of hippocampal-dependent cognitive tasks and for screening a pharmaceutical agent for its ability to modulate performance by an animal of hippocamapl-dependent cognitive tasks.

STAUFEN analogs, or derivatives, are defined herein as proteins having amino acid sequences analogous to the staufen gene products described herein. Analogous amino acid sequences are defined herein to mean amino acid sequences with sufficient identity of amino acid sequence of the staufen gene product described herein to possess the biological activity or biological function or action of the staufen gene product, but with one or more "SILENT" changes in the amino acid sequence.

Biologically active STAUFEN fragments refer to biologically active polypeptide fragments of STAUFEN and can include only a part of the full-length amino acid sequence of STAUFEN, yet possess biological activity of STAUFEN. Such fragments can be produced by carboxyl or amino terminal deletions, as well as one or more internal deletions.

STAUFEN fusion proteins comprise STAUFEN as described herein, referred to as a first moiety, linked to a second moiety not occurring in the STAUFEN protein. The second moiety can be a single amino acid, peptide or polypeptide or other organic moiety, such as a carbohydrate, a lipid or an inorganic molecule.

The present invention further encompasses biologically active derivatives or analogs of STAUFEN, referred to herein as STAUFEN peptide mimetics. These mimetics can be designed and produced by techniques known to those skilled in the art. See, e.g., U.S. Pat. Nos. 5,643,873 and 5,654,276. These mimetics are based on staufen sequences. Staufen sequences are readily available in the art (see, e.g., Shao, et al., *Neuron,* 32:463-475 (2001); Wickham et al., *Mol. Cell. Biol.,* 19(3):2220-2230 (1999); Buchner et al., *Genomics,* 62(1):113-118 (1999); Micklem et al., *EMBO J.,* 19(6):1366-1377 (2000); Monshausen et al., *J. Neurochem.,* 76(1):155-165 (2001); Tang et al., *Neuron,* 32(3):463-475 (2001); Falcon et al., *Nucleic Acid Research,* 27(11):2241-2247 (1999); and Kiebler et al., *J. Neurosci.,* 19(1):288-297 (1999)). Peptide mimetics possess biological activity or biological function or action similar to the biological activity or biological function or action of the corresponding peptide compound, but possess a "biological advantage" over the corresponding peptide inhibitor with respect to one, or more, of the following properties: solubility, stability and susceptibility to hydrolysis and proteolysis.

Methods for preparing peptide mimetics include modifying the N-terminal amino group, the C-terminal carboxyl group and/or changing one or more of the amino linkages in the peptide to a non-amino linkage. Two or more such modifications can be coupled in one peptide mimetic. Examples of modifications of peptides to produce peptide mimetics are described in U.S. Pat. Nos. 5,643,873 and 5,654,276.

Increased STAUFEN protein expression or production can be achieved by administration of an exogenous STAUFEN or, alternatively, by increasing production of the endogenous STAUFEN, for example by stimulating the endogenous gene to produce increased amounts of STAUFEN. In a preferred embodiment, suitable pharmaceutical agents, as described herein, can be administered to the animal to stimulate the endogenous gene to produce increased amounts of a functional STAUFEN, thereby increasing STAUFEN function in the animal.

In some animals, the amount of STAUFEN being produced can be of sufficient quantity, but the STAUFEN is abnormal in some way and, thus, cannot exert its biological effect. That is, the STAUFEN being produced has diminished or no functional activity (i.e., no biological activity, function or action). In this instance, providing copies of normal staufen genes to the animal using techniques of gene transfer well known to those skilled in the art, can increase STAUFEN function or concentration. In another embodiment, an exogenous STAUFEN, STAUFEN analog, biologically active STAUFEN fragment or STAUFEN fusion protein can be administered to the animal.

Nucleic acid sequences are defined herein as heteropolymers of nucleic acid molecules. The nucleic acid molecules can be double stranded or single stranded and can be a deoxyribonucleotide (DNA) molecule, such as cDNA or genomic DNA, or a ribonucleotide (RNA) molecule. As such, the nucleic acid sequence can, for example, include one or more exons, with or without, as appropriate, introns, as well as one or more suitable control sequences. In one example, the nucleic acid molecule contains a single open reading frame which encodes a desired nucleic acid product. The nucleic acid sequence is "operably linked" to a suitable promoter.

A nucleic acid sequence encoding a desired STAUFEN, STAUFEN analog, biologically active STAUFEN fragment or STAUFEN fusion protein can be isolated from nature, modified from native sequences or manufactured de novo, as described in, for example, Ausubel et al., *Current Protocols in Molecular Biology,* (New York: John Wiley & Sons) (1998); and Sambrook et al., *Molecular Cloning: A Laboratory Manual,* 2nd edition (New York: Cold Spring Harbor University Press) (1989). Nucleic acids can be isolated and fused together by methods known in the art, such as exploiting and manufacturing compatible cloning or restriction sites.

Typically, the nucleic acid sequence will be a gene which encodes the desired STAUFEN, STAUFEN analog or STAUFEN fusion protein. Such a gene is typically operably linked to suitable control sequences capable of effecting the expression of the STAUFEN, preferably in the CNS. The term "operably linked", as used herein, is defined to mean that the gene (or the nucleic acid sequence) is linked to control sequences in a manner which allows expression of the gene (or the nucleic acid sequence). Generally, operably linked means contiguous.

Control sequences include a transcriptional promoter, an optional operator sequence to control transcription, a sequence encoding suitable messenger RNA (mRNA) ribosomal binding sites and sequences which control termination of transcription and translation. In a particular embodiment, a recombinant gene (or a nucleic acid sequence) encoding STAUFEN, STAUFEN analog, biologically active STAUFEN fragment or STAUFEN fusion protein can be placed under the regulatory control of a promoter, which can be induced or repressed, thereby offering a greater degree of control with respect to the level of the product.

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. Suitable promoters are well known and readily available in the art (see, e.g., Ausubel et al., *Current Protocols in Molecular Biology* (New York: John Wiley & Sons, Inc.) (1998); Sambrook et al., *Molecular Cloning: A Laboratory Manual,* 2nd edition (New York: Cold Spring Harbor University Press (1989); and U.S. Pat. No. 5,681,735).

STAUFEN, STAUFEN analogs, biologically active STAUFEN fragments, STAUFEN fusion proteins and pharmaceutical agents, as well as nucleic acid sequences encoding STAUFEN, STAUFEN analogs, biologically active STAUFEN fragments or STAUFEN fusion proteins can be administered directly to an animal in a variety of ways. In a particular embodiment, administration is via transplant of neural tissue, e.g., by injecting neural cells into the brain. Other routes of administration are generally known in the art and include intravenous injection including infusion and/or bolus injection, intracerebroventricular, intrathecal, parenteral, mucosal, implant, intraperitoneal, oral, intradermal, transdermal (e.g., in slow release polymers), intramuscular, subcutaneous, topical, epidural, etc. routes. Other suitable routes of administration can also be used, for example, to achieve absorption through epithelial or mucocutaneous linings. STAUFEN, STAUFEN analogs, biologically active STAUFEN fragments and STAUFEN fusion proteins can also be administered by gene therapy, wherein a DNA molecule encoding a particular therapeutic protein or peptide is administered to the animal, e.g., via a vector, which causes the particular protein or peptide to be expressed and secreted at therapeutic levels in vivo.

A nucleic acid sequence encoding a protein or peptide (e.g., STAUFEN, STAUFEN analog, biologically active STAUFEN fragment or STAUFEN fusion protein) can be inserted into a nucleic acid vector according to methods generally known in the art (see, e.g., Ausubel et al., eds., *Current Protocols in Molecular Biology*, John Wiley & Sons, Inc., New York (1998); Sambrook et al., *Molecular Cloning: A Laboratory Manual,* 2nd edition (New York: Cold Spring Harbor University Press) (1989)).

The mode of administration is preferably at the location of the target cells. In a particular embodiment, the mode of administration is to cells of neural origin. Cells of neural origin include neural stem cells, neuroblastoma cells and neurons.

STAUFEN, STAUFEN analogs, biologically active STAUFEN fragments, STAUFEN fusion proteins and pharmaceutical agents, as well as nucleic acid sequences encoding STAUFEN, STAUFEN analogs, biologically active STAUFEN fragments or STAUFEN fusion proteins can be administered together with other components of biologically active agents, such as pharmaceutically acceptable surfactants (e.g., glycerides), excipients (e.g., lactose), stabilizers, preservatives, humectants, emollients, antioxidants, carriers, diluents and vehicles. If desired, certain sweetening, flavoring and/or coloring agents can also be added.

STAUFEN, STAUFEN analogs, biologically active STAUFEN fragments, STAUFEN fusion proteins and pharmaceutical agents, as well as nucleic acid sequences encoding STAUFEN, STAUFEN analogs, biologically active STAUFEN fragments or STAUFEN fusion proteins can be administered prophylactically or therapeutically to an animal prior to, simultaneously with or sequentially with other therapeutic regimens or agents (e.g., multiple drug regimens), including with other therapeutic regimens used for the treatment of long term memory defects, the enhancement of long term memory formation, the modulation of performance of hippocampal-dependent cognitive tasks or the treatment of hippocampal-dependent cognitive task performance defects. STAUFEN, STAUFEN analogs, biologically active STAUFEN fragments, STAUFEN fusion proteins and pharmaceutical agents, as well as nucleic acid sequences encoding STAUFEN, STAUFEN analogs, biologically active STAUFEN fragments or STAUFEN fusion proteins, that are administered simultaneously with other therapeutic agents can be administered in the same or different compositions. Two or more different STAUFEN, STAUFEN analogs, biologically active STAUFEN fragments, STAUFEN fusion proteins, nucleic acid sequences, pharmaceutical agents or combinations thereof can also be administered.

STAUFEN, STAUFEN analogs, biologically active STAUFEN fragments, STAUFEN fusion proteins, and pharmaceutical agents, as well as nucleic acid sequences encoding STAUFEN, STAUFEN analogs, biologically active STAUFEN fragments or STAUFEN fusion proteins, can be formulated as a solution, suspension, emulsion or lyophilized powder in association with a pharmaceutically or physiologically acceptable parenteral vehicle, carrier or excipient. Examples of such vehicles, carriers and excipients are water, saline, Ringer's solution, isotonic sodium chloride solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation can be sterilized by commonly used techniques. Suitable pharmaceutical carriers are described in Remington's Pharmaceutical Sciences.

An effective amount of pharmaceutical agent, STAUFEN, STAUFEN analog, biologically active STAUFEN fragment, STAUFEN fusion protein or nucleic acid sequence is that amount, or dose, administered to an animal that is required to effect a change (increase or decrease) in STAUFEN protein expression or in STAUFEN function. The dosage administered to an animal, including frequency of administration, will vary depending upon a variety of factors, including pharmacodynamic characteristics of the particular augmenting agent, mode and route of administration; size, age, sex, health, body weight and diet of the recipient; nature and extent of symptoms being treated or nature and extent of the cognitive function(s) being enhanced or modulated, kind of concurrent treatment, frequency of treatment, and the effect desired.

Pharmaceutical agents, STAUFEN, STAUFEN analogs, biologically active STAUFEN fragments, STAUFEN fusion proteins and nucleic acid sequences can be administered in single or divided doses (e.g., a series of doses separated by intervals of days, weeks or months), or in a sustained release form, depending upon factors such as nature and extent of symptoms, kind of concurrent treatment and the effect desired. Other therapeutic regimens or agents can be used in conjunction with the present invention. Adjustment and manipulation of established dosage ranges are well within the ability of those skilled in the art.

Once an effective amount has been administered, a maintenance amount of a pharmaceutical agent, STAUFEN, STAUFEN analog, biologically active STAUFEN fragment or STAUFEN fusion protein, or nucleic acid sequence encoding a STAUFEN, STAUFEN analog, biologically active STAUFEN fragment or STAUFEN fusion protein, can be administered to the animal. A maintenance amount is the amount of pharmaceutical agent, STAUFEN, STAUFEN analog, biologically active STAUFEN fragment or STAUFEN fusion protein (or nucleic acid sequence encoding a STAUFEN, STAUFEN analog, biologically active STAUFEN fragment or STAUFEN fusion protein) necessary to maintain the change (increase or decrease) in STAUFEN protein expression or in STAUFEN function achieved by the effective dose. The maintenance amount can be administered in the form of a single dose, or a series or doses separated by intervals of days or weeks (divided doses). Second or subsequent administrations can be administered at a dosage which is the same, less than or greater than the initial or previous dose administered to the animal. Determination of such amounts are well within the ability of those skilled in the art.

The present invention will now be illustrated by the following examples, which are not to be considered limiting in any way.

EXAMPLES

Example 1

Staufen Expression in Mouse Hippocampus

A fragment of mouse staufen, from nucleotide 551 to 851 of sequence AF061942 from the NCBI database, was amplified by polymerase chain reaction (PCR) and subcloned into a EcoRI site of a PCRII vector (InVitroGen).

Antisense probes were generated by cutting the PCRII subclone with SmaI, priming from the Sp6 promoter. Sense probes were generated by cutting the PCRII subclone with BglII, priming from the T7 promoter.

Brains of 8-10 week old male wild type C57Bl/6 mice were surgically removed and placed in liquid nitrogen. Brains were sliced on a cryostat at 16 um and allowed to air dry. Tissue sections then were subjected to the following in situ hybridization protocol:

Day 1:

If sections from fixed brains were used, the sections were sent to the prehybridization washes step. If fresh-frozen brains (i.e., not fixed) were used, the sections were first fixed as follows:

Fixing Fresh-Frozen Sections:

Slides were immersed in 4% paraformaldehyde/1×PBS at 4° C. for 20 min. The sections were then sent to prehybridization washes.

Prehybridization Washes:

1. The slides were washed 2×5 minutes with 1×PBS (pH 7.4)

2. The slides were then washed 2×5 minutes with 1×PBS containing 100 mM glycine, freshly made since it will precipitate if made ahead of time.

3. The slides were then incubated 15 minutes with 1×PBS containing 0.3% Triton X-1100.

4. The slides were then washed 2×5 minutes with 1×PBS.

Permeabilization:

5. Pre-warmed TE buffer, pH 8.0 (100 mM Tris-HCl, pH 8.0, 50 mM EDTA, pH 8.0) at 37° C. was used. The slides were incubated 20 minutes at 37° C. with TE buffer, pH 8.0, containing 1 µg/ml Proteinase K (RNase-free).

Post-Fix:

6. The slides were incubated 5 minutes at 4° C. in 4% paraformaldehyde/1×PBS.

7. The slides were then wash 2×5 minutes with 1×PBS.

Acetylation:

8. The slides were incubated and rocked 2×5 minutes with 0.1 M triethanolamine (TEA) buffer, pH 8.0, containing 0.25% (v/v) acetic anhydride which has been added immediately before incubation.

Pre-Hybridization:

9. Slide hybridization chambers were placed over sections on slide. Pre-hybridization buffer was pre-warmed (4×SSC, 50% formamide) at 37° C. About 750 µl were pipetted in per slide. The slides were incubated at 37° C. for 10 min. or more.

Hybridization:

10. Hybridization solutions were prepared using Ambion In Situ Hyb Buffer (Ambion #8806G) and 0.5-1 µg of DIG-labeled riboprobe per ml. Enough hyb buffer plus probe was prepared for about 750 µl per slide. These solutions were kept on ice.

11. Pre-hybridization buffer was removed with pipet and about 750 µl of hyb buffer plus probe was pipetted into hyb chamber. The slides were laid out in a humid chamber. The humid chamber was sealed tightly and the slides were incubated overnight at 42° C.

Day 2:

Posthybridization:

12. Slides were kept separated according to probe, removed from the hyb chambers, then washed 2×15 minutes in 2×SSC, with shaking at 37° C.

13. The slides were washed 2×15 minutes with 1×SSC, with shaking at 37° C.

14. RNasing—At this point, slides with different probes could be put together. NTE buffer (500 mM NaCl, 10 mM Tris, pH 8.0, 1 mM EDTA, pH 8.0) to 37° C. was pre-warmed. Slides were incubated for 30 minutes at 37° C. in NTE buffer containing 20 µg/ml RNase A.

15. 0.1×SSC was prewarmed to 37° C. The slides were washed 2×30 minutes in 0.1×SSC, with shaking at 37° C.

Immunological Detection:

16. Slides were washed 2×10 minutes in Buffer 1 (100 mM Tris-HCl, pH 7.6, 150 mM NaCl), with shaking at RT.

17. New hyb chambers were placed on slides, and blocking solution was added (Buffer 1 with 2% normal sheep serum and 0.1% Triton X-100) about 750 µl per slide. The slides were incubated for 30 minutes in blocking solution.

18. The blocking solution was removed with pipet and about 750 µl of antibody solution (0.1% Triton X-100, 1% sheep serum, 1:1000 anti-DIG-alkaline phosphatase) was gently pipetted in. The slides were placed in a humid chamber and either incubated for 2 hours at room temperature (RT), or overnight at 4° C.

19. Hyb chambers were removed, then the slides were washed 2×10 minutes in Buffer 1 with shaking at RT.

20. The slides were incubated for 10 minutes in Buffer 2 (100 mM Tris-HCl, pH 9.5, 100 mM NaCl, 50 mM $MgCl_2$).

21. The slides were incubated in color solution (1× NBT/BCIP, 1 mM levamisole) for 2-24 hours in the dark (NBT=4-nitro blue tetrazolium chloride; BCIP=5-bromo-4-chloro-3-indolyl-phosphate). When color development was optimal, the color reaction was stopped by incubating the slides in Buffer 3 (10 mM Tris-HCl, pH 8.0, 1 mM EDTA, pH 8.0), then the slides were dipped in distilled water. Counterstaining could be done on the slides using 0.1% Nuclear Fast Red (in water), about 5 minutes incubation. The slides were incubated 2×10 minutes in distilled water.

After mounting tissue, DIG-labeled sections were viewed with an Axioplan 2 imaging microscope from Ziess for expression in the hippocampus and adjoining areas.

Staufen expression was detected throughout the hippocampus with antisense RNA probes. Expression also was detected in other regions of the brain. In particular, antisense RNA probe hybridized to cells in the CA1, CA3 and dendate gyrus regions. In contrast, sense (control) probes yielded no detectable signal. These results imply that interference with staufen function vis RNA antisense injections into the hippocampus will disrupt memory formation.

The following materials and methods were used in the work described in Example 2.

Animals and Surgery

Ten to twelve week old C57B1/6 male mice (Taconic Laboratory, N.Y.) were used. Mice were housed in groups of four in standard mouse cages and kept in a 12:12 light-dark cycle and constant temperature (22° C.) in a humidity and ventilation-controlled animal house. With the exception of surgery, training and testing times, the mice had ad lib access to food and water. Animals were acclimatized to animal house environment for a week before surgery. On a day of surgery, mice were anesthetized with 20 mg/kg Avertin and implanted with a 26-gauge guide double cannula aimed at the dorsal hippocampus using a stereotaxic apparatus (Korf Instruments, Calif.; coordinates: P=1 mm; L=1.5 mm to a depth of 1-1.2 mm; Franklin and Paxinos, *The Mouse Brain In Stereotaxis Coordinates*, Academic Press, San Diego, Calif. (1997)). After the end of surgery, animals were individually maintained in a cage with ad lib access to food and water. Seven days after recovery from surgery, animals were trained for contextual fear conditioning.

Fear Conditioning Experiments

The basic fear conditioning procedures and equipment remained as described (Bourtchuladze, R. et al., *Cell*, 79:59-68 (1994); and Bourtchouladze et al., *Learn Mem.*, 5(4-5): 365-374 (1998)). On the training day, the mouse was placed in the conditioning chamber (Med Associates) for 2 minutes before the onset of unconditioned stimulus (US) of 0.5 mA, two seconds shock. For weak training, US was repeated two times with a one minute inter-trial interval between shocks. For strong training, 5 USs were given. Training was automated and performed by computerized software package (Med Associates).

Thirty seconds after the end of the last trial, the mouse was returned to its home cage. The conditioning chamber was cleaned with 75% ethanol and then with water. Contextual memory was tested four days after training by scoring freezing responses. Freezing was assessed with a sampling method. That is, 2 second observations were taken every 5 seconds (Bourtchuladze, R. et al., *Cell*, 79:59-68 (1994); Bourtchouladze et al., *Learn Mem.*, 5(4-5):365-374 (1998); and Frankland, P. W. et al., *Behav. Neurosci.*, 112:863-874 (1998)). A mouse was determined to be freezing when it adopted a motionless posture, refraining from all but respiratory movements.

For each training and drug-injecting procedure, an experimentally nave group of animals was used. The observations were made by an experimenter unaware of the experimental treatment of the mice. In each experiment, both training and testing were videotaped. Experiments were analyzed with an analysis of variance (ANOVA) and t-tests.

Drug and Oligodeoxynucleotide (OND) Infusion Procedures

Anisomycin (ANI) (Sigma) was dissolved in 0.9% saline, and the pH was adjusted with 1 N HCl to 7.4. Control animals received injections of saline. Mice were injected in the hippocampus (62.5 µg/2 µl per hippocampus) immediately after training. Infusions were made through the guide cannula using a 33-gauge injection needle. The needle was connected via a polyethylene tube to a microsyringe fixed in the pump 11 (Harvard Instruments). The entire infusion procedure took 2 minutes and animals were freely moving during this time in the home cage. Experiments were replicated 2 times and for each training procedure, an experimentally nave group of animals was used (n=47 total).

Mouse antisense oligodeoxynucleotides (ODNs) directed against CREB mRNA (5'-T-s-g-s-g-s-T-C-A-T-T-T-g-T-T-A-C-C-g-s-g-s-T-s-g-3') (SEQ ID NO: 1) was used to disrupt hippocampal CREB protein levels. Control groups received infusions of ODN of the same base composition but in randomized order (scrambled CREB: 5'-g-s-T-s-C-s-T-g-T-A-g-T-C-g-A-T-C-T-A-T-s-g-s-g- -s-T-3') (SEQ ID NO:2). ODNs were administered into the hippocampus (2 nmol/2 µl per hippocampus) as described above for ANI-infusion. CREB ODNs were infused 20 hours before training. Experiments were replicated 3 times and for each training procedure, an experimentally nave group of animals was used (n=54 total).

Mouse antisense oligodeoxynucleotides (ODNs) directed against staufen mRNA (5-'g-s-g-s-g-s-C-T-T-A-T-A-C-A-T-T-g-s-g-s-T-s-T-3') (SEQ ID NO:3) were used to disrupt hippocampal STAUFEN protein levels. Control groups received infusions of ODN of the same base composition but in randomized order (scrambled staufen: 5'-g-s-T-s-g-s-T-A-C-T-g-A-T-T-g-A-C- -s-T-s-g-s-T-3') (SEQ ID NO:4). ODNs were administered into the hippocampus (4 nmol/2 µl per hippocampus) as described above for ANI-infusion. Staufen ODNs were infused repeatedly, 3 times. The first infusion was made 44 hours before training. The second infusion was made 15 hours before training. The third infusion was made immediately after training. Experiments were replicated 3 times and for each training procedure, an experimentally nave group of animals was used (n=39 total).

Histology

After the end of the behavioral testing, 2 µl of a solution of 4% methylene blue was infused into the cannula. Animals were sacrificed and their brains were removed, frozen and then cut at −20° C. with cryostat for histological localization of infusion cannula.

Example 2

STAUFEN and Long Term Memory Formation In Mice

Figure 1:
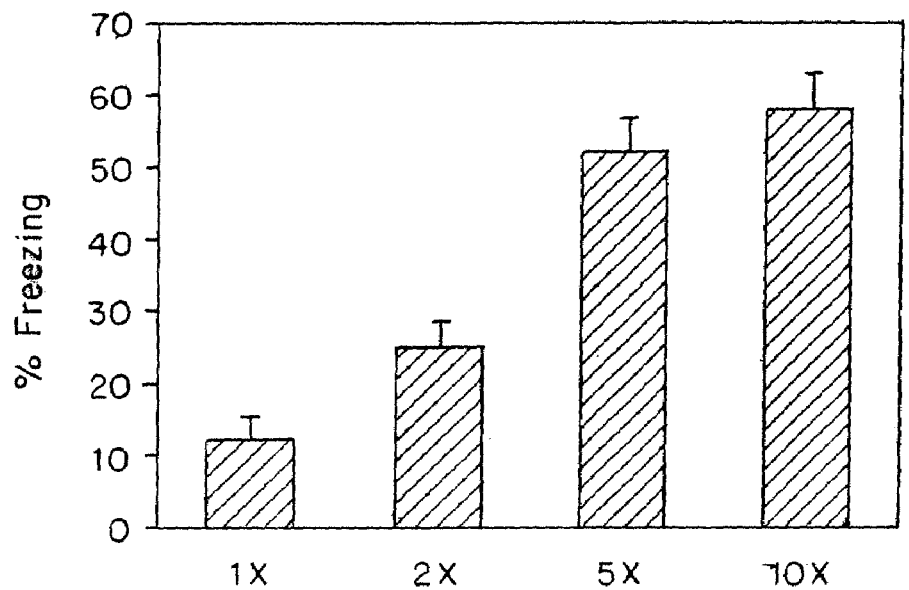
FIG. 1 is a bar graph representation of the effect on memory in mice four days after training in a contextual fear conditioning task. Mice were trained with 1, 2, 5 or 10 training trials (1×, 2×, 5× and 10×; 0.5 mA shock for 2 seconds; n=22, n=20, n=19 and n=22 animals, respectively). 5× yields maximal levels of long-term memory, which is not significantly different from memory induced by 10× (P>0.05). 2× yields less than half maximal levels (P<0.001 for 2× vs. 5×).

Five training trials (5ב'strong" training) yields maximal levels of long term memory, while two training trials (2ב'weak" training) yields less than half maximal levels (FIG. 1).

Figure 2:
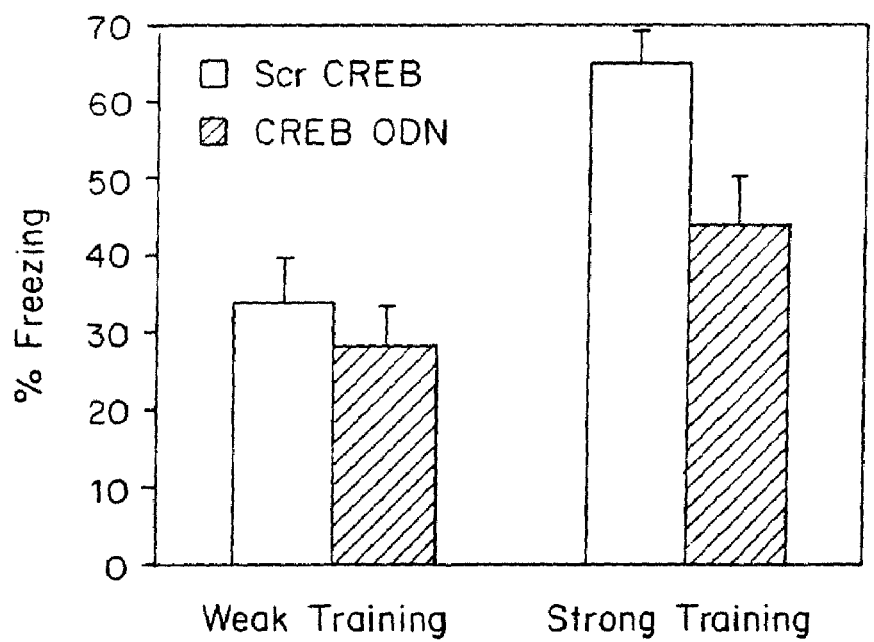
FIG. 2 is a bar graph representation of the effect of CREB oligodeoxynucleotides (ODNs) treatment on memory in mice after training. CREB ODNs decreased memory induced by strong training (5 trials) to the levels produced by weak training (2 trials). CREB ODNs or scrambled CREB were delivered into the hippocampus (2 nmol/2 µl) 20 hours before training mice with weak (2 trials) or strong training (5 trials). Mice were tested 4 days after training. CREB ODNs significantly impaired memory induced by strong training (p<0.01; n=17 and n=14 for CREB ODNs- and scrambled CREB-injected animals, respectively) but had no effect on the memory levels produced by weak training (p=0.47; n=12 and n=11 for CREB ODNs- and scrambled CREB-injected animals, respectively).

Partial knock down of CREB expression by injection of antisense oligonucleotides into the hippocampus 20 hours before training reduced memory induced by strong training to the levels produced by weak training (FIG. 2). CREB ODN-injected mice showed significantly less freezing responses than vehicle-injected mice when animals were trained with 5USs (65.1±4.3% and 44.2±6.3%, control- and CREB ODN-injected mice, n=14 and n=17, respectively; p<0.01) (FIG. 2). There was no significant difference between CREB ODN- and vehicle-injected mice when mice were trained with 2 USs, although freezing responses of CREB ODN-treated mice were less than controls (34±5.8% and 28.4±5.1%, n=11 and n=12, respectively, p=0.47). These results provided validation of "CREB-dependence" for the assay.

Figure 3:
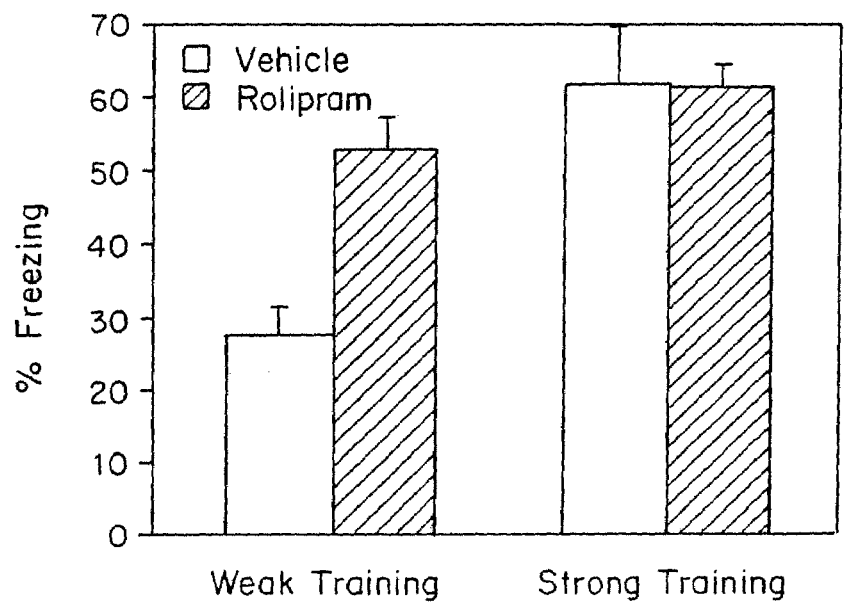
FIG. 3 is a bar graph representation of the effect of Rolipram treatment on memory in mice after weak training in a contextual fear conditioning task. Memory is enhanced in C57B16 mice by Rolipram after weak training in a contextual fear conditioning task. Rolipram or vehicle were delivered into the hippocampus (30 ng/1 µl per hippocampus) immediately after training mice with weak (2 trials) or strong training (5 trials). Mice were tested 4 days after training. Rolipram significantly enhanced memory induced by weak training (p<0.001; n=12 and n=24 for Rolipram and vehicle injected animals, respectively) but had no effect on the maximal memory levels produced by strong training (p=0.93; n=8 and n=13 for drug and vehicle injected animals, respectively). Similarly, injection of 3 ng Rolipram produced memory enhancing effect on weak training (p<0.005; n=16). However, 0.03 ng Rolipram had no memory enhancing effect (p<0.42; n=8).

The prototypical type-IV phosphodiesterase inhibitor, Rolipram, administered immediately after training, significantly enhanced the amount of memory induced by weak training but had no effect on the maximal memory levels produced by strong training. These experiments provided further support for "CREB-dependence" for the assay (FIG. 3).

Figure 4:
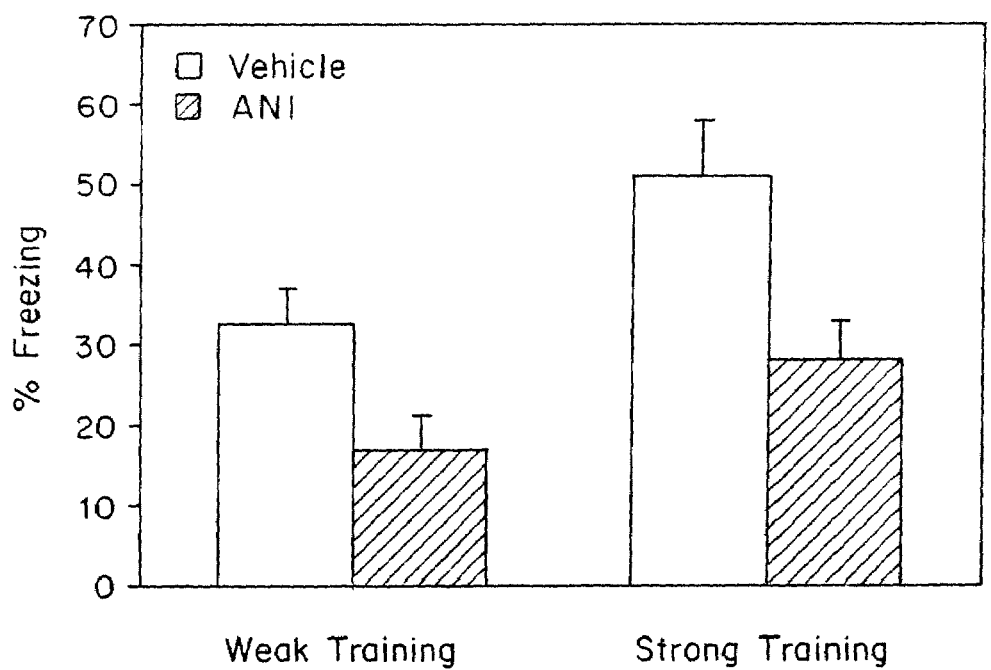
FIG. 4 is a bar graph representation of the effect of anisomycin (ANI) treatment on memory in mice after training. Contextual conditioning memory is anisomycin sensitive. ANI (62.5 mg/2 µl per hippocampus) or vehicle was delivered into the hippocampus immediately after training. Mice were tested 4 days after training. ANI significantly impaired memory induced strong (p<0.01; n=13 and n=11 for ANI- and vehicle-injected mice, respectively) or weak training (p<0.05; n=10 and n=12 for ANI- and vehicle-injected mice, respectively).

Protein synthesis inhibitor anisomycin (ANI), injected immediately after training, blocked contextual memory (FIG. 4). ANI-injected mice showed significantly fewer freezing responses than vehicle-injected mice when animals were trained with 5USs (51.01±7% and 28.42±4.9%, control- and ANI-mice, n–11 and n=13, respectively; p<0.01) or 2USs (32.7±4.4% and 17.1±4.3%, control- and ANI-mice, n=10 and n=12, respectively; p<0.05).

Figure 5:
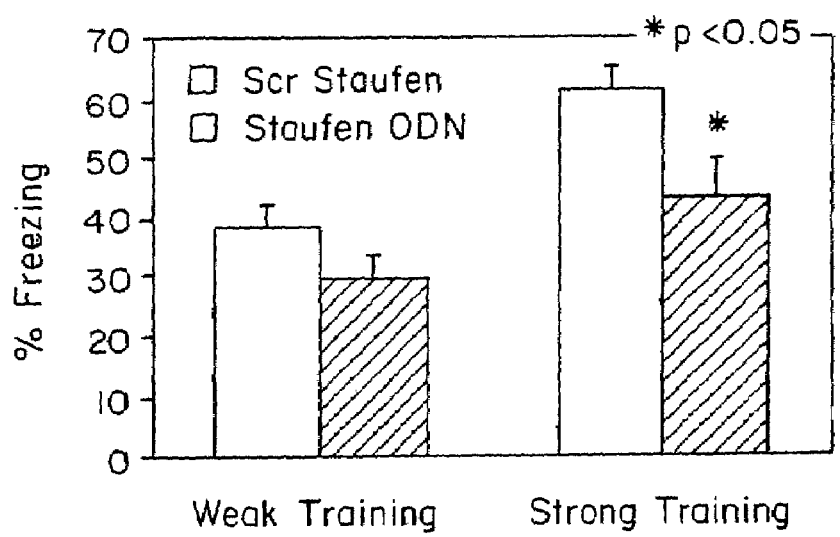
FIG. 5 is a bar graph representation of the effect of staufen ODNs treatment on memory in mice after training. Staufen ODNs impair 4-day memory in mice. Staufen ODNs or scrambled staufen were delivered into the hippocampus (4 nmol/2 ml per hippocampus, 44 hours and 15 hours before training, and immediately after training. Staufen ODNs significantly impaired memory induced by strong training (p<0.05; n=12 and n=10 for staufen ODNs and scrambled staufen-injected animals, respectively) but had no significant effect on the memory produced by weak training (p=0.08; n=7 and n=10 for staufen ODNs and scrambled staufen-injected animals, respectively).

Staufen antisense ODN treatments impaired 4-day retention in mice after 5 US training (FIG. 5). Freezing responses of staufen-treated mice (42.8±6.6%, n=12) were significantly less (p<0.05) than vehicle-injected mice (61±5%, n=10). There was no significant difference between staufen- and vehicle-injected mice when mice were trained with 2 USs, although freezing responses of staufen-treated mice were less than controls (30±3.1% and 38.4±3.0%, n=10 and n=7, respectively, p=0.08).

Together, these results indicate that different training protocols—weak and strong training-recruit shared and distinct molecular processes for contextual memory formation. Maximal levels of memory, induced with strong training, require protein synthesis that is matched by a requirement of cAMP-signaling, CREB-dependent transcription and normal function of STAUFEN in the hippocampus (most likely in somata). Memory induced by weak training appears to recruit protein synthesis in CREB- and STAUFEN-independent fashion; perhaps, through local protein synthesis pools in dendrites.

The following materials and methods were used in the work described in Examples 3 to 5.

Behavioral Training and Genetic Strains

Olfactory associative learning was quantified by subjecting two-to-three day old adult flies to a Pavlovian conditioning procedure (Tully, T. et al., *Cell*, 79:35-47 (1994); and Tully, T. and Quinn, W. G., *J. Comp. Physiol. [A]*, 157:263-277 (1985)). Briefly, groups of about 100 flies were exposed sequentially to one odor (CS+) paired with footshock and then a second odor (CS−) without foot-shock. Spaced and massed trained animals received 10 such training sessions with a 15-minute rest interval between sessions in the case of spaced training. For DNA chip experiments, animals were rapidly frozen immediately (t=0), six (t=6) or 24 hours (t=24) after training. 10 massed training sessions are completed in 39 minutes, compared with 2 hours 51 minutes for 10 spaced training sessions. To control for this timing difference, all groups of flies were loaded into machines at the same time, but onset of massed training was delayed such that completion of both training regimens were simultaneous. Groups experiencing massed training thus experienced the training context (including air current) for the same total duration as the spaced-trained groups. During the test trial (FIG. 6), flies were exposed simultaneously to the CS+ and CS− in a T-maze. After two minutes, flies were trapped in either T-maze arm, anesthetized and counted. From this distribution, a performance index (PI) was calculated, so that a 50:50 distribution (no memory) yielded a PI of zero and a 0:100 distribution away from the CS+yielded a PI of 100. PIs were distributed normally and, hence, were analyzed parametrically. For DNA chip and QPCR follow up experiments, an isogenic white line (w$^{1118}$(isoCJ1)) (Yin, J. C. et al., *Cell*, 81:107-115 (1995)) was used. StauC8/stauD3 heteroallelic mutants were generated by crossing b,pr,stau$^{C8}$/Cy0 and cn,stau$^{D3}$/Cy0 flies.

Affymetrix Chip Hybridizations and Probe Preparation

Total cellular RNA was isolated from adult heads using Trizol reagent (Gibco-BRL manufacturer's protocol). Frozen tissue was dolfed in a mortar and then dounce homogenized in Trizol using a glass homogenizer (5 ml Trizol/gram tissue). Biotinylated cRNA probes for Affymetrix chip hybridizations were generated according to Affymetrix protocols. Reverse transcription was carried out using an anchored oligo-DT primer containing a T7 RNA polymerase sequence (5'-GGCCAGTGAATTG TAATACGACTCACTATAGGGA GGCGG-T$_{24}$-VN-3') (SEQ ID NO:5). cRNA (10 μg) probes were resuspended in 200 μl hybridization solution: 0.1 mg/ml herring sperm DNA, 0.5 mg/ml acetylated BSA, 0.1 M MES (Sigma MES-hydrate and MES-sodium salt), 1.0 M NaCl, 0.01% Triton X-100. Hybridization reactions, labeling, and chip scanning were done according to Affymetrix protocols.

Statistical Analysis

"Average Difference" (AvDif) values for each gene from each chip were obtained from Affymetrix software without regard to any other parameter therein. The following steps of data analysis then were performed:

1) For a given timepoint (N=10 chips for spaced and 10 chips for massed), all AvDif values below 10 were eliminated from the database (set to "missing values).

2) The remaining AvDif values on each chip were normalized to the mean AvDif for all genes and chips, $$NormAvDiff = AvDif_{ij} \times \frac{\text{Mean } AvDif}{\text{Mean } AvDif_j}$$

for gene $i$ on chip $j$.

3) All genes for which N=0 (because of eliminated values) for spaced OR massed treatments were eliminated.

4) A BoxCox transformation was performed (Westfall, P. H. and Young, S. S., Resampling-based Multiple Testing: Examples and Methods for p-value Adjustment (New York: John Wiley & Sons, Inc.) (1993)) on NormAvDif values, according to a two-way analysis of variance (ANOVA) model with TREATMENT and GENE as main effects and TREAT x GENE as the interaction term. This method evaluates a family of transformations of BoxAvDif=NormAvDif$^x$, where −1<X<1 to find the particular value of X that minimizes the Sums of Squares Error (SSE) of the ANOVA model (Sokal, R. R. and Rohlf, F. J., Biometry, 2nd edition (San Francisco: W.H. Freeman) (1981)).

5) All genes for which N<3 for spaced OR massed treatments were eliminated.

6) The Effect Size (ES) for each gene was calculated as:

ES=mean BoxAVDIF (spaced)−mean BoxAvDif (massed).

7) The statistical significance of each ES was determined via a bootstrapping method with the critical value (alpha) set at 0.05.

8) For comparisons across different experiments (timepoints) ES values were expressed as Standard Normal Deviates (StNDs) as follows:

$$StD = \frac{ES_i}{St. Dev \cdot ES}$$

for genes i and where St.Dev is the standard deviation of the mean ES.

Quantitative Polymerase Chain Reaction (QPCR)

RNA isolations were performed with Trizol (BRL) as for Affymetrix chip probe preparation (see above) with the following modifications. After the Trizol step, samples were treated with DNAaseI (Promega-5U per sample) for 30 minutes (37° C.) and then were extracted with phenol/chloroform/iso-amyl alcohol (BRL), precipitated with ethanol and resuspended in DEPC-treated water. Reverse transcription reactions were performed using 2.5 µG RNA per reaction with an oligo dT primer using Taqman reverse transcription reagents (Applied Biosystems). PCR quantification was performed using 10% of the above RT product per reaction on a 7,700 real-time PCR machine using (Perkin Elmer) and SYBR green PCR core reagents (Applied Biosystems) according to manufacturer's protocols. Prior to QPCR, all PCR products were verified by either restriction mapping or automated sequencing. Gene specific primers had the following sequences: pum: 5'-TGTAGACATAGTCTGGGGTC-CTC-3' (SEQ ID NO:6) and 5'-AAGCAACAGCCAT-TGGGTCCAC-3' (SEQ ID NO:7), dCREB2: 5'-GCAACTCGTCGGCGGC ATC-3' (SEQ ID NO:8) and 5'-CGCCGGGCCGTTGTA CTTTGT-3' (SEQ ID NO:9), rux: 5'-CCACTCTGATTCCGCCACTG-3' (SEQ ID NO: 10) and 5'-GCGTTGAATCCTCCTCGGTATC-3' (SEQ ID NO: 11), TBP: 5'-GCGGCTGTGATTATGCGAAT-3' (SEQ ID NO: 12) and 5'-CATACTTTCTC GCTGCCAGTCTG-3' (SEQ ID NO: 13), slbo: 5'-CAGACTACCGATGCGAACA ACA-3' (SEQ ID NO: 14) and 5'-GTGCCTGAACTGGTG-GTGTATCA-3' (SEQ ID NO: 15), gliotactin: 5'-CGCCT-TCTGGAGGCAATACT-3' (SEQ ID NO: 16) and 5'-GC-GATCTGTAGTGGCTCCTTG-3' (SEQ ID NO: 17). Expression levels were normalized to *Drosophila* TBP transcript levels. TBP was confirmed as an unchanged control by comparing in excess of 100 RNA extractions each after spaced and massed training. Thus TBP was a false positive at t=6 in these DNA chip experiments. All reactions were done in parallel using at least 8 independent RNA isolations for each group, with each RNA isolate being assayed in triplicate.

Immunocytochemistry and Confocal Imaging

Whole mount immunolabeling of adult brains was performed according to Chiang et al., 2001 (Chiang, A. S. et al., *J. Comp. Neurol.*, 440:1-11 (2001)) using a Rat-anti-PUM antibody originally tested for specificity using Western blots from mutant animals (Sonoda, J. and Wharton, R. P., *Genes Dev.*, 13:2704-2712 (1999)). Briefly, dissected brains were fixed for two hours in a room temperature vacuum and then overnight with 4% paraformaldehyde in PBS. Fixed tissue then was blocked for two days at 4° C. in PBS containing 2% Triton-X and 10% normal goat serum (NGS) and then successively incubated for 2 days each (with washing in between) at 4° C. in PBS containing 1% Triton X, 0.25% NGS and (1) a polyclonal rat anti-pum antibody (Sonoda, J. and Wharton, R. P., *Genes Dev.*, 13:2704-2712 (1999)) diluted 1/1000, (2) a biotinylated goat anti-mouse IgG (1:200) and (3) a strepavidin CyS-conjugate (1 µg/ml, diluted 1000.times. from stock solution) in PBS containing 1% Triton-X. Next, tissue was treated with RNAse (0.1 mg/ml) for one hour, stained overnight in NBD (0.435 mM) (Chiang, A. S. et al., *J. Comp. Neurol.*, 440:1-11 (2001)), for 30 minutes in propidium iodide (0.00625 mg/ml) and then mounted in FOCUSCLEAR. Whole-mount brains were imaged with a Zeiss LSM 510 confocal microscope (Carl Zeiss, Jena), equipped with a 10× Fluor objective lens (N.A. 0.5, working distance 2000 µm) and a 40× C-Apochromat water immersion objective lens (N.A. 1.2, working distance 220 mm).

Example 3

Experimental Design and Statistical Analysis for DNA Microarrays

Transcriptional responses to olfactory LTM are likely to occur in a small subset of neurons of the adult brain. One brain region critically involved in olfactory learning and memory is the mushroom body (de Belle, J. S, and Heisenberg, M., *Science*, 263:692-695 (1994); Dubnau, J. et al., *Nature*, 411: 476-480 (2001); Pascual, A. and Preat, T., *Science*, 294:1115-1117 (2001); Zars, T. et al., *Science*, 288:672-675 (2000)), which consists of approximately 5,000 neurons or roughly 10% of the brain. Since mRNA is extracted from whole heads, a significant reduction in the signal from transcripts responding to memory formation is expected. Thus, a statistical method which optimizes the detection of small-magnitude differences in transcript levels was developed as described below.

The nalvot$^{P1}$ mutation disrupts LTM and produces a two-fold reduction in the level of expression of ADF1, a transcription factor apparently involved in structural but not functional aspects of synaptic plasticity (DeZazzo, J. et al., *Neuron*, 27:145-158 (2000)). Thus, Adf-1 served as an internal positive control by comparing basal transcript levels between control (wildtype) flies and nalyot mutants using a prototype *Drosophila* DNA chip from Affymetrix containing 1,542 known, cloned genes. An experimental design was employed that (i) balanced various sources of variation across treatment groups (wildtype versus mutant) and (ii) increased the number of replicate chips to improve statistical power. Traditional parametric statistics were optimized to detect reliably the Adf-1 difference. The optimal method is as follows: (1) 1,000 heads were used per RNA extract, thereby averaging any individual variation (from genetic background or other epigenetic effects) and any batch effects (from handling sub-groups of animals on different days). (2) A minimum of 5 replicate chips (independent RNA extractions) were used per treatment group. (3) "Avg-Diff" values less than 10 were eliminated. (4) Avg-Diff values on each chip were normalized for small differences in the amounts of probe used per chip. (5) A Box-Cox transformation was applied to Normalized Avg-Diff values to minimize the experiment-wide error variance (sums of squares error, SSE) and to yield more homogeneous error variances among groups (genes). (6) Statistical significance for the effect size (ES; the difference between mean values for wild-type versus mutant treatment) for each gene was determined via bootstrapping. (7) Effect sizes for all genes then were expressed as "standard deviates" (sdv; the effect size for a given gene expressed in units of the standard deviation of all ESs (for all genes).

This method yielded a significant difference for expression of Adf-1 transcripts between wildtype flies and nal$^{P1}$ mutants (ES=2.8 sdv; N=5; P=0.002). The decrease in Adf-1 expression in nalyot mutant flies was confirmed with real-time (quantitative) RT-PCR (QPCR; N=4 RNA extracts; P=0.001) and with Northern blots (N=12 RNA extracts; P=0.001).

Another gene on the chip, annotated as "CaSpeR-1" in the Affymetrix database, expressed at significantly higher levels in nal$^{P1}$ mutants than in wildtype flies (ES=−4.1 sdv.). The specific oligonucleotide (oligo) sequences on the chip corresponded to the "mini-white" eye color marker gene contained within the PlacW transposon insertion of the nal$^{P1}$ mutation (DeZazzo, J. et al., Neuron, 27:145-158 (2000)). In fact, the wildtype control flies (white$^{1118}$) carry a deletion of this region of the white gene. Hence, another internal control was detected on the chip that is expressed in mutant flies but not in wildtype control flies.

Overall, 68 of 1,542 genes showed statistically significant differences between wildtype and nal$^{P1}$ flies, with effect sizes (absolute values) ranging from 0.3 to 5.1. When ranking these effects from highest to lowest, the "CasPer-1" gene was fourth and Adf1 was sixth. The largest effect size for the photolyase gene (FBgn0003082) was also confirmed via Northern blot analysis.

When compared to this parametric method, the traditional 2-fold approach differs in two important ways. First is the "denominator effect": A majority of candidates from the 2-fold method are relatively low-expressing genes. This occurs because smaller effect sizes are needed to yield a 2-fold change when the denominator of the ratio is a smaller number. Second is the "false negative effect": A majority of candidates identified from the parametric method were higher-expressing genes that were not detected by the 2-fold approach. This observation indicates that many biologically relevant changes in transcript expression levels might be missed with the traditional 2-fold method. This comparison is a relative one; each statistical method also has its own implicit false-positive rate. Similar issues regarding the traditional two-fold analysis have been echoed in emerging literature on the statistical analysis of DNA microarray data (Jin, W. et al., Nat. Genet., 29:389-395 (2001); Schadt, E. E. et al., J. Cell. Biochem., 80:192-202 (2000); Van Der Laan, M. J. and Bryan, J., Biostatistics, 2: 445-461 (2001); and Wolfinger, R. D. et al., J. Comput. Biol., 8:625-637 (2001)).

Example 4

Identification of Candidate Memory Genes (CMGs)

Previous studies have yielded a genetic dissection of olfactory memory formation in Drosophila (Tully, T. et al., Cell, 79:35-47 (1994); Dubnau, J. and Tully, T., Annu. Rev. Neurosci., 21:407-444 (1998); Tully, T., Proc. Natl. Acad. Sci. USA, 93:13460-13467 (1996); and Waddell, S, and Quinn, W. G., Annu. Rev. Neurosci., 24:1283-1309 (2001)). Of particular relevance is the observation that the long-lasting memory produced by spaced training (10 training sessions with a 15 minute rest interval between each) is blocked when protein synthesis is inhibited (Tully, T. et al., Cell, 79:35-47 (1994)) or when expression of a CREB repressor transgene is induced (Yin, J. C. et al., Cell, 79:49-58 (1994)). Both of these manipulations produce no effect on memory after massed training (10 training sessions with no rest intervals). These results indicate that the memory produced in normal flies after spaced training, above and beyond that after massed training, is critically dependent on (CREB-mediated) gene expression. Thus, comparing mRNA from wildtype flies subjected to spaced versus massed training should identify transcriptional changes specific to LTM. For example, non-specific transcriptional effects produced by exposure to odors or foot-shock alone are likely to be present after both spaced and massed training, thereby yielding no differential effect.

To accomplish this DNA chip comparison, approximately 60,000 wild-type flies were subjected to spaced or massed training in a balanced experimental design using batches of approximately 100 flies per training run. One hundred batches of flies (10,000 individuals) were frozen in liquid nitrogen at each of three time-points (t=0, 6 and 24 hours) after spaced or massed training. These 100 batches of frozen flies were combined, heads were collected and then distributed randomly into 10 sets of approximately 1,000 to generate 10 independent RNA extracts (for each time point and training regimen). In this manner, potential variations among different training runs or among individual flies (because of genetic background differences or other epigenetic effects) were averaged out leaving only the potential treatment effects of spaced and massed training. These 10 replicate RNA extractions then were used to generate probes for hybridization to 10 independent Affymetrix DNA chips. Importantly, inclusion of 10 replicates in this experimental design ensured a proper sampling of variation derived from separate RNA extractions (which were estimated to be nearly 40 times greater than the variation due to replicate chip hybridizations using the same cDNA).

From these data, 129 candidate memory genes (CMGs) were identified using the statistical method described herein in Example 3: 47 from t=0, 26 from t=6 and 58 from t=24 hour groups (two genes were significant at two time points each).

False positives are inherent in all DNA chip experiments, regardless of statistical method. Hence, only a subset of these CMGs will prove to be true positives. Follow-up QPCR assays can be done on independent samples of RNA to identify true positives.

Most, if not all, genes are pleiotropic, with protein functions that subserve more than one biological process. For example, a cell cycle gene that functions as a kinase to regulate cytoskeletal elements during mitosis also may phosphorylate different substrates in terminally differentiated neurons (Mendez, R. et al., EMBO J., 21:1833-1844 (2002)). Thus, CMGs that initially do not appear to be involved in memory formation, nevertheless, may participate in memory formation (Pinto, S. et al., Neuron, 23:45-54 (1999)).

Confirmation that a CMG is involved in memory formation rests with the demonstration that in viva modulation (disruption) of the gene alters that process (with some specificity). To this end, the pum gene has been identified two independent times (a CMG both at t=0 and t=6) from a behavioral screen for memory mutants with defective one-day memory after spaced training. Mutations in pum produce deficits in one-day memory after spaced training, and pum is transcriptionally regulated in normal flies during long-term memory formation. The former result constitutes confirmation of pum as a CMG that was suggested by the DNA chip experiments. The latter result indicates that pum participates in a cellular process that is acutely required during memory formation in the adult.

Existing polyclonal antibodies (Sonoda, J. and Wharton, R. P., Genes Dev., 13:2704-2712 (1999)) were used to determine the expression pattern of PUM in the central nervous system (CNS) of normal adults. Immunolabeling with a polyclonal rat-anti-PUM antibody (Sonoda, J. and Wharton, R. P., Genes Dev., 13:2704-2712 (1999)) decorates somatic regions of most neurons. PUM was found to be expressed broadly with a complex subcellular distribution. The majority of PUM immunoreactivity is peri-nuclear, but significant punctate staining also is observed in neuropilar regions. For example, in the mushroom bodies, strong somatic staining surrounds the nucleus of all intrinsic neurons (Kenyon cells). Weaker punctate expression is detected in the dendritic neuropil region of the mushroom bodies (calyx). These observations suggest that PUM may function widely in the CNS.

Similar results were obtained on 5 μM sections as well as in whole mount preparations with a polyclonal rabbit-anti-PUM antibody (Sonoda, J. and Wharton, R. P., *Genes Dev.*, 13:2704-2712 (1999)), with or without pre-absorption against embryonic tissue.

First discovered in genetic screens for mutations affecting *Drosophila* embryonic development, the pum gene is part of a pathway involved in translational repression during posterior patterning and germline determination (Johnstone, O. and Lasko, P., *Annu. Rev. Genet.*, 35:365406 (2001); and Palacios, I. M. and Johnston, D. S., *Annu. Rev. Cell. Dev. Biol.*, 17:569-614 (2001)). Polarization of the antero-posterior axis of the oocyte involves microtubule-dependent transport to the posterior pole of a large RNP complex known as a "polar granule", containing nanos (nos) mRNA, as well as numerous additional components, including the CMGs staufen, oskar, nago nashi and faf. Localized nos message serves as a restricted source of NOS protein, which functions together with PUM to repress translation of several target mRNAs. Other genetic components in xenopus or fly oocytes that interact with PUM/NOS to regulate translation include cytoplasmic polyadenylation element binding protein (CPEB or orb in flies) (Nakahata, S. et al., *J. Biol. Chem.*, 276:20945-20953 (2001)), CycB, cdc2 (as a dimer, the latter two show kinase activity which phosphorylates orb, thereby targeting it for ubiquitin-mediated degradation) (Mendez, R. et al., *EMBO J.*, 21:1833-1844 (2002); and Reverte, C. G. et al., *Dev. Biol.*, 231:447-458 (2001)), the ubiquitin-proteosome pathway and eIF4-E (the cap-binding protein). Phosphorylation of CPEB by aurora kinase also facilitates interaction of eIF4-E with eIF4-G and the rest of the translation initiation complex (Stebbins-Boaz, B. et al., *Mol. Cell.*, 4:1017-1027 (1999)). Known PUM/NOS target mRNAs include CycB (Nakahata, S. et al., *J. Biol. Chem.*, 276:20945-20953 (2001); and Asaoka-Taguchi, M. et al., *Nat. Cell Biol.*, 1:431-437 (1999)) and sex lethal (Sxl) (Deshpande, G. et al., *Cell*, 99:271-281 (1999)).

Both the DNA chip experiments described here and a complementary behavioral screen for memory mutants (e.g., see Example 2) have identified several components of this pathway. In addition to pum, DNA chip analyses have yielded stau, mago, faf orb and Sxl as CMGs. Moreover, another CMG, msl-2, is a known translational target of Sxl. Several other CMGs appear to be involved more generally in the cellular machinery subserving RNA binding, regulation of translation and cytoskeletal function. Only one of these CMGs (pumilio) was identified using the traditional 2-fold method of microarray analysis, thereby providing some biological validation for this statistical method.

These findings are further convergent with those of the complementary behavioral screen for memory mutants in which P element insertions have been identified in or near pum, oskar, eIF-5C, CycB and seven additional genes involved with RNA processing and cytoskeletal function. These findings suggest that the cellular machinery involved in targeting mRNAs and locally regulating their translation during embryogenesis also may be used by neurons during long term memory formation.

Example 5

Disruption of Staufen after Training Interferes with Long Term Memory Formation In *Drosophila*

In vertebrate hippocampal neurons, STAUFEN protein is associated with a large RNP complex known as a "neural granule" (Krichevsky, A. M. and Kosik, K. S., *Neuron*, 32:683-696 (2001); Tang, S. J. et al., *Neuron*, 32:463-475 (2001); Kiebler, M. A. et al., *J. Neurosci.*, 19:288-297 (1999); and Kohrmann, M. et al., *Mol. Biol. Cell.*, 10: 2945-2953 (1999)). Neural granules are thought to package newly transcribed mRNAs with translational repressors and ribosomal components. These RNP particles then are transported via microtubules along dendritic shafts, where they appear to disassemble in response to specific postsynaptic depolarizations presumably to release their repressed mRNAs for local, activity-dependent translation of new proteins (Steward, O. and Schuman, E. M., *Annu. Rev. Neurosci.*, 24:299-325 (2001); Krichevsky, A. M. and Kosik, K. S., *Neuron*, 32:683-696 (2001); Tang, S. J. et al., *Proc. Natl. Acad. Sci. USA*, 99:467-472 (2002); and Aakalu, G. et al., *Neuron*, 30:489-502 (2001)).

Identification with DNA chips and a behavioral screen (e.g., see Example 2) of multiple components of this cellular machinery suggests the involvement during memory formation of neural granules in the delivery of CREB-dependent transcripts to recently activated synapses. A direct prediction from this hypothesis is that disruption of staufen after training will interfere with long-term memory formation.

Figure 6:
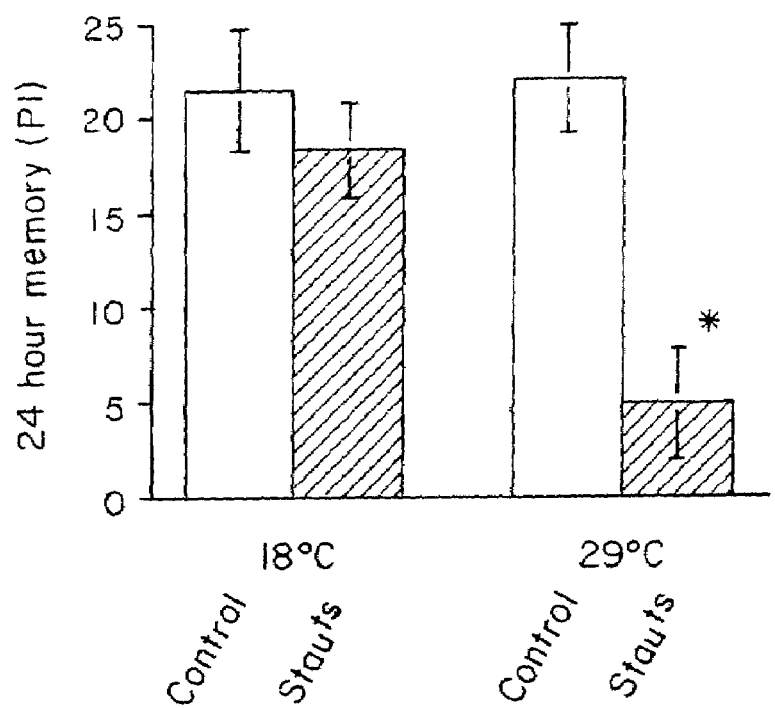
FIG. 6 is a bar graph representation showing 24 hour memory in *Drosophila* after spaced training in wildtype controls and temperature-sensitive staufen mutants. Memory was assessed using a Pavlovian assay (Tully, T. et al., *Cell*, 79:35-47 (1994); and Tully, T. and Quinn, W. G., *J. Comp. Physiol. [A]*, 157:263-277 (1985)) in which an odor (CS) is paired with a footshock (US). One-day memory after spaced training is equivalent in wildtype controls and temperature-sensitive staufen (stau$^{C8}$/stau$^{D3}$) mutants when animals were trained, stored during the 24 hour retention interval, and tested at the permissive temperature (P=0.44 (18° C.)). In contrast, one-day memory after spaced training was disrupted specifically in stau mutants (P<0.001) when they were trained and tested at permissive temperature but were shifted to restrictive temperature (29° C.) during the retention interval. N=16 PIs per group.

To test this hypothesis, memory formation was assayed in a temperature-sensitive mutant of staufen (stau$^{C8}$/stau$^{D3}$) (Ephrussi, A. et al., *Cell*, 66:37-50 (1991); and Lehmann, R. and Nusslein-Volhard, C., *Development*, 112:679-691 (1991)). At the restrictive temperature (29° C.), stau$^{C8}$/stau$^{D3}$ mutant embryos exhibit a strong mutant phenotype (a complete deletion of abdominal patterning, along with other defects). However, at permissive temperature (18° C.), only slight defects in abdominal segmentation can be seen. Accordingly, when these stau$^{C8}$/stau$^{D3}$ mutants were raised at the permissive temperature, and then adults were subjected to spaced training, stored during the retention interval and tested for one-day memory all at permissive temperature, memory scores were comparable to controls reared under the same conditions (FIG. 6). In contrast, when these mutants were raised, trained and tested at permissive temperature but were transiently shifted to restrictive temperature only during the retention interval, one-day memory was nearly abolished (FIG. 6). Importantly, this transient disruption of staufen does not produce non-specific effects on learning or on sensorimotor responses because performance levels are similar (P=0.92, N=6 PIs per group) in staufen mutants when they are trained and tested at 18° C. (PI=41±5) or when they first are shifted to 29° C. for one-day prior to training and testing immediately after being returned to 18° C. (PI=40±6). These latter controls rule out the possibility that non-specific effects on sensorimotor responses to odors or footshock underlie the observed defects in memory retention produced by this transient disruption of STAUFEN. Rather, these data demonstrate an acute requirement for STAUFEN after training—during the consolidation of long-term memory.

The following materials and methods were used in the work described in Example 6.

Breeding of Mutant Strains

Transposon mutagenesis was carried out as described (Dura, J. et al., *J. Neurogenet.*, 9:1-14 (1993)) with minor modifications. A PGAL4 transposon or a PlacZ X-linked mutator was used to generate strains "A-D" and "E", respectively, which carried homozygous, adult-viable transposon insertions somewhere on the second or third chromosomes (autosomes). At maximum effort, 96 mutant strains were generated and screened each week. After N=5 experiment, those strains with reproducibly defective memory (see below) were outcrossed for at least five generations to the parental strain to equilibrate genetic backgrounds. For A-D strains, this parental strain was w$^{1118}$; Sp/CyO;Sb/TM3, Ser double-balancer stock, which itself had been outcrossed to our standard W$^{1118}$ (isoCJ1) stock. For E strains, the parental strain was W$^{1118}$ (isoCJ1) itself.

Behavioral Screen

Pavlovian olfactory conditioning: One to four day old adult flies were placed in dry food bottles the night before training and kept at 25° C. Environment-controlled rooms remained at a constant 25° C. with 70% humidity, and flies were trained/tested in the dark. During one training session, a group of approximately 100 flies was exposed consecutively to octanol (CS+) paired with footshock (US) and then to a methylcyclohexanol (CS−) without footshock, piped through the training chamber in an air current. For spaced training, flies were subjected to ten training sessions with a 15-minutes rest interval in between each. Flies then were placed in dry food vials overnight at 18° C. The next day, conditioning odor avoidance responses were assessed for two minutes in a T-maze, where the CS+ and CS− are delivered simultaneously on convergent currents of air. After testing, flies were trapped in their respective T-maze arms, anesthetized and counted. A performance index (PI) was calculated so that a 50:50 distribution (no memory) yielded a PI of 0 and a 0:100 distribution away from the CS+ yielded a PI of 100. For one complete experiment, a second group of 100 flies was trained with odor2 as the CS+ and odor1 as the CS−, and the two resulting PIs were averaged for an N=1.

One-day memory after spaced training was evaluated for mutant strains in a minimum of three passes. On the first pass, an N=1 was generated for a strain. If the resulting PI was <50% of normal (wild-type) levels, then an N=4 PIs was generated in a second pass. [At the maximum effort, 96 mutant strains were evaluated each week, and the 17 lowest-scoring strains were chosen for the second pass; their scores still were ≦50% of wild-type controls.] If the average PI≦70% of normal, then the strain was outcrossed to equilibrate genetic backgrounds (see above), re-homozygosed, and a second N=4 PIs was generated in a third pass. If the average PI again was <70%, then the strain was designated a candidate memory mutant, and task-relevant sensorimotor responses were evaluated.

Sensorimotor Responses: Shock reactivity was carried out in the T-maze according to (Tully, T. et al., Cell, 79:35-47 (1994)). Two copper grids were attached to either arm while only one was electrified (60 V). PIs were calculated as above by designating the shocked T-maze arm as "CS+". Olfactory acuity was carried out in the T-maze according to a previously published procedure herein incorporated by reference (Tully, T. et al., Cell, 79:3547 (1994)). The relative avoidance of octanol versus methylcyclohexonal (delivered at the concentrations used during conditioning) was quantified for nave flies. PIs were calculated as above by arbitrarily designating one odor as "CS+". A minimum of N=6 PIs were generated for each sensorimotor response. Sixty candidate mutant strains yielded average PIs≧90% of wild-type controls and were designated as memory mutants. Two additional strains (D0107 and D0185) yielded average PIs for olfactory acuity <75%, with those for shock reactivity still ≧90%, of controls. These were designated olfactory mutants. In a similar fashion, two strains (E3029 and E3065) were designated shock reactivity mutants.

Learning: Memory retention immediately after a single training session also was quantified in the 60 memory mutants. Average PIs were ≦90% of controls for 10 strains; these strains were distinguished as "learning" mutants, rather than "memory" mutants, although the distinction is somewhat arbitrary.

Molecular Identification of Transposon Mutations

Plasmid rescue of transposons: Genomic DNA was isolated from homozygous mutant flies, digested to completion with one of several possible restriction enzymes (mainly EcoRI, SacI and XhoI) and "plasmid rescued" using standard protocols (Sullivan, W. et al. (Eds.), Drosophila Protocols (Cold Spring Harbor Laboratory Press, Cold Spring Harbor) (2000)). Sequences were obtained by automated sequencing (ABI) using a primer directed against the 3' LTR of pGawB or PlacZ (5-CACTCGCACTTAT TGCAAGCATACG-3') (SEQ ID NO: 18) and were compared to the FlyBase annotated database of Drosophila genome sequence (6 Gelbart, W. M. et al., Nucleic Acids Res., 25:63-66 (1997)). In every successful case (57 of 60), a unique genomic insertion site was determined. For two strains (D0264 and D0851), the DNA sequence appeared identical, but it corresponded entirely to sequences internal to PGAIL4. Consequently, a genomic insertion site(s) has not yet been identified for these strains.

"Dog-tagging": To confirm the molecular identification of each genomic insertion site and to identify each memory mutant unambiguously, a rapid PCR-based method was developed to detect the transposon insertion unique to each mutant strain. From the genomic sequence around the transposon insertion site, three PCR primers were generated. The sequence of one primer corresponded to the (common) 5' end of the transposon; the sequences of the other two primers then corresponded to genomic sequence flanking the (unique) transposon insertion site. The PCR reaction then was run with all three primers. In each case, the choice of genomic primer sequences was such that fragments of two discernable sizes were PCR-amplified. A "mutant" fragment appeared if genomic DNA contained the appropriate transposon insertion. Alternatively, "wild-type" fragment appeared of genomic DNA did not contain the appropriate transposon insertion (i.e., from wild-type flies or from an inappropriate transposant strain). Flies (or populations) heterozygous (heterogeneous) for the appropriate transposon insertion were identified by the presence of both the mutant and wild-type PCR fragment. Genomic DNA from a given strain was obtained with standard methods.

For PCR, one 1 μl of each genomic sample was added to a PCR tube, and 1 μl of the appropriate primer was then added. The addition of 5 μl of PCR buffer, 1.5 μl of magnesium chloride, 35.5.μl of distilled water, 1 μl of DNTP's, and 0.5 μl of Taq was added to all samples. Thirty rounds of ampflication were run at the appropriate annealing temperatures for each primer. The PCR samples were then electrophoresed on an 1% agarose gel. For initial characterizations, the appropriate bands (mutant and wild-type) were gel purified and restriction-digested to confirm that the amplified bands were of the expected sequence. Such dog-tag confirmation was accomplished for all 57 strains described.

Northern Blot Analyses of CMGs

RNA was isolated (according to manufacturer's protocols) with Trizol (Gibco) from heads of four independent groups of flies for each strain. PolyA RNA was selected using oligo dT-magnetic beads (Dynal) according to the manufacturer's protocol. Northern blots were prepared using standard techniques (DeZazzo, J. et al., Neuron, 27:145-158 (2000)). Briefly, 5 μg of PolyA-RNA per sample were electrophoresed through a 1% agarose-formaldehyde gel using MOPS buffer. Gels were blotted onto nylon membrane (Schleicher and Schuel). P-32 labeled probes were generated by random priming using PCR-fragments corresponding to each CMG (which either were sequenced or restriction digested to confirm the fidelity of amplification).

Enhancer-Trap Reporter-Gene Histology of Memory Mutants

PlacZ: Freshly dissected brains from 2-5 day-old flies were fixed in freshly prepared 0.2% glutaraldehyde in PBS for 10 minutes on ice. Brains are washed 3× in PBS for 5 minutes each at room temperature (RT). Brains are incubated in XGAL staining solution (2 mg XGAL/1 ml XGAL buffer) in a moist, sealed container for 5 minutes to 48 hours at 37° C. Brains are post-fixed in 4% paraformaldehyde and 0.1% Triton-X 100 in PBS for 30 minutes in vacuum at RT (allow air in and out several times for best results). Brains were cleared in FocusClear™; the FocusClear™ bottle was kept in a hot water bath. Brains were mounted in MountClear™ (from the hot-water bath). Whole-mount brains were photographed on a Zeiss dissecting scope, using a SV11 objective.

PGAL4: Homozygous mutant females were bred to homozygous UAS-GFPS$^{S65T}$ males (Bloomington stock #1521). The mushroom body enhancer trap strain, C747, was used as a positive control, while homozygous mutant females (no UAS-GFP) served as negative controls. Three-to-five day old heterozygous female progeny were examined for GFP expression patterns. Flies were anesthetized with $CO_2$ and quickly dissected while pinned to a Sylgard-covered dish and submerged in PBS. The proboscis was pushed carefully into the extended position with fine forceps, a patch of cuticle on the posterior of the proboscis was removed, and the large silvery tracheae within the head capsule were carefully peeled out, avoiding damage to brain. The eyes to the level of the lamina were then carefully removed and the brain was immaculately cleaned of all external tracheae using two fine forceps. Brains were carefully transferred to 4% paraformaldehyde for 30 minutes, then to 4% paraformaldehyde +0.25% Triton-X 100 for 30 minutes under mild vacuum. Brains were then cleared using FocusClear™ solution (Pacgen, Vancouver, Canada) for 5 minutes, and then mounted in a drop of the same solution (Chiang, A. S. et al., *J. Comp. Neurol.*, 440:1-11 (2001)).

Whole-mount brains were imaged with a Zeiss LSM 510 confocal microscope (Carl Zeiss, Jena), equipped with a 10× Fluar objective lens (N.A. 0.5, working distance 2000 μm) and a 40× C-Apochromat water immersion objective lens (N.A. 1.2, working distance 220 μm). Structures with GFP expression were excited with a Kr/Argon laser at 488 nm, and their fluorescence was detected after emissions had passed through a 505 nm long-pass filter. Stacks confocal images were taken through the full thickness of the central brain. The images were stored at a size of 1024×1024 pixels. The distance between successive images (Z-axis distance) was adjusted for the refractive index mismatch of the air and mounting medium as described previously (Chiang, A. S. et al., *J. Comp. Neurol.*, 440:1-11 (2001)). In some cases, frontal and dorsal projections were rendered using Amira 2.3 (TGS, Inc., San Diego) after removing optical slices between brain surface and mushroom bodies to better reveal internal structures.

Example 6

Behavioral Screen for Memory Mutants

A large-scale behavioral screen for memory mutants was conducted one day after spaced training. The behavioral screen was initiated using a genetically engineered P element transposon (carrying a either a GAL4 or beta-GALACTOSIDASE enhancer-trap reporter gene) as a mutator (Boynton, S, and Tully, T., *Genetics,* 131:655-672 (1992); and Dura, J. et al., *J. Neurogenet.,* 9:1-14 (1993)). A total of 6,681 homozygous-viable transposants were generated, each carrying (usually) a single P element insertion somewhere on the 2nd or 3rd chromosomes (which comprise about 80% of the *Drosophila* genome). One-day memory after spaced training was quantified for each strain. One hundred and six strains showed an average PI (performance index)≦70% of wild-type control flies after at least five generations of outcrossing to the genetic background of wild-type control flies. Sensorimotor responses to the odors and footshock used during Pavlovian training then were evaluated. Sixty strains showed PIs≧90% of wild-type control flies both for olfactory acuity and for shock reactivity (cf. Dura, J. et al., *J. Neurogenet.,* 9:1-14 (1993)). Thus, these 60 strains represent new mutants with behavioral defects specific to the associative component of olfactory long-term memory. These memory mutants were named after Pavlov's dogs.

Memory immediately after a single training session also was evaluated for these 60 memory mutants to judge whether "learning" was defective along with one-day memory after spaced training. The PIs of ten mutants were <90% of wild-type controls, indicating defects in both initial learning and in one-day memory after spaced training. Of the remaining 50 mutants, 9 were judged "weak" memory mutants with PIs between 51% and 70% of controls, while 41 were judged to be "strong" memory mutants with PIs≧50%. In the course of these genetic crosses and behavioral assays, it was discovered that three of the latter memory mutants were homozygous-lethal but nevertheless yielded memory defects as heterozygotes.

Because the entire DNA sequence of the *Drosophila* genome now is available, it was possible to rapidly identify the molecular lesions for 57 of these 60 mutant strains. These 57 lesions define 49 sites in the *Drosophila* genome. Twenty five of these sites lie within, and 24 lie between, defined transcription units (genes), thereby identifying a total of 70 new candidate memory genes (CMGs). Among these CMGs are four genes, oskar, CyclinB, eIF-5C and pumilio, which are known to be involved in the translocation of mRNA and regulation of translation during embryogenesis. Significantly, pumilio and several other genetic components (staufen, mago nashi, fat facets, orb, cdc2 and eIF2-G) of this cellular machinery also have been identified as transcriptionally regulated genes during long-term memory formation in normal (wild-type) *Drosophila*. The milord, norka, avgust and kravavietz enhancer-trap mutations all show reporter-gene expression in adult mushroom bodies, as do a majority of the other mutant strains. More interestingly, however, a few mutant strains show enhancer-trap patterns of expression outside of mushroom bodies, thereby revealing novel regions of the adult central nervous system that may be involved in olfactory memory formation.

Among the known genes, pumilio was identified twice in the behavioral screen for memory mutants (milord-1 and -2). Significantly, pumilio also was identified from DNA chip experiments on wild-type flies as a transcriptionally regulated CMG at two different time-points (t=0 and t=6 hr) after spaced training. These results are fully complementary. Identifying memory mutants with transposon insertions in the pumilio transcription unit confirms the gene as a "true positive" from the DNA chip experiments. Identifying pumilio in wild-type flies as a transcriptionally regulated gene during long-term memory formation shows that the gene is actively involved in adult neural plasticity.

This initial convergence on pumilio has been reinforced by the observation that additional genetic components of this pathway also have been identified from the behavioral screen and from the DNA chip experiments. Genes that interact with pumilio have been described in the context of embryonic development. Together, they define a biological pathway involved with subcellular localization of mRNAs and local regulation of translation. Several of these interacting genes, including staufen, mago nashi, fat facets, orb, cdc2 and eIF-2G, have been identified from DNA chip experiments. Consistent with this result, three more genetic components of this pathway—oskar, CyclinB and eIF-5C—were CMGs from the behavioral screen for memory mutants (norka, avgust and krasavietz, respectively).

The pumilio, oskar, CyclinB and eIF-5C genes are likely CMGs disrupted in milord-1/-2, norka, avgust and krasavietz memory mutants. For milord-1/-2 and krasavietz, transposon insertions were found to reside within the respective pumilio and eIF-5C transcription units, while the transposons associated with norka and avgust reside near the CycB and oskar genes and disrupt their transcription. The pumilio, staufen, mago nashi, fat facets, orb, cdc2 and eIF-2G genes, which are known to interact with each other, were identified directly from DNA chip experiments as a transcriptionally regulated genes during long-term memory formation. The discovery that mutations of pumilio yield defects in one-day memory, as shown herein, constitutes strong initial proof that pumilio is actively involved in long-term memory formation. The observation that multiple genetic components of this pathway have been identified cross-validates both the DNA microarray experiment and the behavioral mutant screen for identifying genes associated with long-term memory formation.

Convergence beyond the "pumilio pathway" and the "staufen pathway" also is suggested from these two approaches. The mutant screen described herein has identified several CMGs involved in ubiquitin-dependent protein degradation, a cellular process already shown to participate in long-term synaptic plasticity in Aplysia and in *Drosophila* (Hegde, A. N. et al., *Cell*, 89:115-126 (1997); and DiAntonio, A. et al., *Nature*, 412: 449-452 (2001)). In Xenopus oocytes, local translation is controlled in part via phosphorylation of cytoplasmic polyadenylation element binding protein (CPEB; orb is the fly homolog) by CDC2 kinase (Reverte, C. G. et al., *Dev. Biol.*, 231:447-458 (2001)). To this end, DNA chip experiments also identified as a CMGfatfacets (faf), a gene that is known to interact with other members of the "pumilio pathway" or "staufen pathway". The faf gene encodes a ubiquitin C-terminal hydrolase that negatively regulates proteolysis in several development contexts including the larval neuromuscular junction (DiAntonio, A. et al., *Nature*, 412: 449-452 (2001); and Hochstrasser, M., *Curr. Opin. Cell. Biol.*, 7:215-223 (1995)).

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of screening for or identifying a pharmaceutical agent capable of modulating staufen function comprising the steps of:
   a) stimulating the CREB pathway of a neuron expressing a STAUFEN::indicator fusion protein, wherein the STAUFEN::indicator fusion protein is expressed from a DNA construct, which is operably linked to a promoter sequence, that is introduced into the neuron;
   b) measuring the STAUFEN function in the neuron;
   c) introducing a pharmaceutical agent of interest into the neuron, and
   d) measuring STAUFEN function,
   wherein a difference in the STAUFEN function measured in d) compared to the STAUFEN function of neurons of b) to which said pharmaceutical agent has not been administered identifies the pharmaceutical agent as one capable of modulating STAUFEN function, and
   wherein the STAUFEN function is measured by a step selected from the group of detecting the level of STAUFEN::indicator fusion protein expression, detecting the level of STAUFEN::indicator fusion protein mRNA produced, detecting the level of STAUFEN::indicator fusion protein produced, detecting trans location of STAUFEN::indicator fusion protein into dendrites, measuring downstream gene products regulated by a staufen gene product, and determining the distribution of neural granules in the cells.

2. The method of claim 1 wherein the indicator is selected from the group comprising luminescent molecules, β-galactosidase, β-glucoronidates, β-glucosidase, and auxitrophic markers.

3. The method of claim 1 wherein the promoter sequence is the promoter sequence of a ubiquitously expressed gene.

4. The method of claim 1 wherein the STAUFEN::indicator fusion protein is expressed transiently in the neurons.

5. The method of claim 1 wherein the neuron is mammalian.

* * * * *